(12) United States Patent
Douglas et al.

(10) Patent No.: US 10,722,165 B1
(45) Date of Patent: Jul. 28, 2020

(54) SYSTEMS AND METHODS FOR REACTION MEASUREMENT

(71) Applicant: BioMech Sensor LLC, Midlothian, VA (US)

(72) Inventors: John Douglas, Richmond, VA (US); Igor Perić, Barcelona (ES); Frank Fornari, Midlothian, VA (US)

(73) Assignee: BioMech Sensor LLC, Midlothian, VA (US)

( * ) Notice: Subject to any disclaimer, the term of this patent is extended or adjusted under 35 U.S.C. 154(b) by 0 days.

(21) Appl. No.: 16/588,596

(22) Filed: Sep. 30, 2019

(51) Int. Cl.
| | | |
|---|---|---|
| *G09B 19/00* | (2006.01) | |
| *A61B 5/16* | (2006.01) | |
| *G06F 3/01* | (2006.01) | |
| *G06F 3/0484* | (2013.01) | |
| *A61B 5/11* | (2006.01) | |
| *A61B 5/00* | (2006.01) | |
| *G06K 9/00* | (2006.01) | |

(52) U.S. Cl.
CPC .......... *A61B 5/162* (2013.01); *A61B 5/1124* (2013.01); *A61B 5/163* (2017.08); *A61B 5/6825* (2013.01); *A61B 5/746* (2013.01); *A61B 5/748* (2013.01); *G06F 3/013* (2013.01); *G06F 3/04842* (2013.01); *G06K 9/00281* (2013.01); *G09B 19/00* (2013.01); *A61B 2562/0219* (2013.01)

(58) Field of Classification Search
CPC ....... A61B 5/162; A61B 5/163; A61B 5/1124; A61B 5/6825; A61B 5/746; A61B 5/748; A61B 2562/0219; G06F 3/013; G06F 3/04842; G06K 9/00281; G09B 19/00
USPC ........................................................ 434/236
See application file for complete search history.

(56) References Cited

U.S. PATENT DOCUMENTS

2016/0262608 A1* 9/2016 Krueger ............... A61B 3/0041
2017/0004358 A1* 1/2017 Bose ....................... G06T 7/251

* cited by examiner

*Primary Examiner* — Robert P Bullington
(74) *Attorney, Agent, or Firm* — Finnegan, Henderson, Farabow, Garrett & Dunner LLP

(57) ABSTRACT

This disclosure relates to systems, media, and methods for quantifying and monitoring visual acuity, motor skill, and cognitive ability of a user through measuring user activities while the user responds to prompts on an electronic device. Disclosed embodiments may receive image data from a user-facing camera, motion data from a sensor device attached to the user, location data from a touchscreen, and time data measuring a user's response times. Disclosed embodiments may provide graphical user interfaces to which the user responds and calculate health metrics based on characteristics of the user's response. Disclosed embodiments may calculate visual acuity, motor skill, and cognitive ability metrics based on data measured while the user responds to the graphical user interfaces. Disclosed embodiments may include comparing the metrics to respective baseline values and providing an alert when the metrics deviate from threshold values indicating a change in user health.

22 Claims, 11 Drawing Sheets

SYSTEMS AND METHODS FOR REACTION MEASUREMENT

TECHNICAL FIELD

This disclosure relates generally to data acquisition and analysis, and more particularly to methods and systems measuring parameters that aid in assessing the health of a user by measuring user responses to graphical user interfaces.

BACKGROUND

Existing methods of measuring reaction time to measure a user's visual acuity, motor skills, and cognitive ability are conducted sequentially. For example, a user may need to perform a separate eye test, physical movement test, and memory test in order for healthcare professionals to assess the user's vision, movement, and memory. Additionally, each of these tests may be conducted by different healthcare professionals, thereby complicating a holistic assessment of the user's health. Furthermore, existing tests of cognitive ability focus on a user's ability to memorize items or follow complicated instructions. Therefore, simple to follow tests that measure a user's cognitive ability as a reaction time to a stimulus, rather than memory, while simultaneously measuring the user's visual acuity and motor skills is needed to aid healthcare professionals in assessing patients.

SUMMARY

Disclosed embodiments may include methods, systems, and computer-readable media to provide a system for measuring reaction times of users. Disclosed embodiments may include an electronic device having a touchscreen, a camera facing a user, at least one memory storing instructions, and at least one processor; and a first sensor device attached to the user, the first sensor device having an inertial measurement unit. The user may follow instructions to perform a simple reaction test. The instructions may include selecting a button when a letter appears on the touchscreen. The processor may execute instructions to enable the simple reaction test, such as operations that include providing, on the touchscreen, a graphical user interface with at least one user-selectable button; updating, at an interval, the graphical user interface to provide at least one letter related to the button; and receiving a user selection on the graphical user interface of the touchscreen. Additionally, the operations may include recording, between the updating and the receiving, data such as image data, from the user-facing camera or any other available camera, including at least a portion of a face of the user; first motion data, from the first sensor device, representing first motions of the user; location data, from the touchscreen, representing a location of the user selection within the graphical user interface; and time data, indicating a time period between the updating and the receiving. Furthermore, the processor may execute instructions to perform operations including determining, based on the location data, if the user performed instructions comprising selecting the selection region on the touchscreen when at least one corresponding object appears; calculating, based on the image data, a visual acuity metric as an average percent of a field of view of the camera that includes the user's face; calculating, based on the first motion data, a motor skill metric as an average amount of time the user moves between the updating and the receiving; calculating, based on the time data, a cognitive ability metric as an average time period between the updating and the receiving, comparing the visual acuity metric, motor skill metric, and cognitive ability metric to a visual acuity threshold, motor skill threshold, and cognitive ability threshold, respectively; and providing, based on the comparing, an alert notifying a healthcare professional when at least one of the visual acuity metric, motor skill metric, or cognitive ability metric exceeds the respective threshold.

In further embodiments, the visual acuity metric, motor skill metric, and cognitive ability metric may be stored. The system may set baseline values of the metrics as respective averages of stored metrics, and set thresholds based on the respective baseline values. The embodiments may further include waiting for a predefined period, such as a short delay, before updating the graphical user interface with a new letter giving the user another test screen. In some embodiments, the system may provide a user-entry field that receives a user entry in order to set the predefined period. Additionally, the embodiments may include randomly determining the waiting period by choosing from a range of durations, where the range is predefined.

In further embodiments, the system may update the graphical user interface to display the letter in a different size and color from the previous displayed letter. The system may then calculate the visual acuity metric taking into account the size and color of the letters. Additionally, disclosed embodiments may use the first motion data to determine a number of accelerations that the user performed over a threshold, and calculate the motor skill metric on the basis of the number of accelerations, thereby quantifying the user's jerky or shaky movements. In still further embodiments, the system may update the graphical user interface to provide a display corresponding to instructions having a difficulty level, where the difficulty level is based on the number of letters that are shown on the screen. The cognitive ability metric may also be calculated based on the difficulty level.

In some disclosed embodiments, the system may identify the user's pupils in images recorded by the camera. Using the locations of the user's pupils, the system may determine where the user is looking and calculate an amount of time that the user spends looking at the touchscreen or specific portions thereof. The cognitive ability metric may be calculated on the basis of the amount of time the user spends looking at the touchscreen or specific portions thereof. The system may also ask if the user is wearing eyeglasses and identify the user's eyeglasses in the image. The system may calculate where the user is looking based on the location of the user's eyeglasses in the image, calculate an amount of time the user spends looking at the touchscreen, and calculate the cognitive ability metric based on an amount of time that the user spends looking at the touchscreen or specific portions thereof.

In still further embodiments, the system may also include a second sensor device, having an inertial measurement unit, that is worn on the user's right hand. The user may also wear the first sensor device on the user's left hand. The user may follow instructions that specify which hand must be used when selecting buttons on the screen. The system may also record second motion data from the second sensor device, representing a second motion of the user; determine if the user performed the instructions with the correct hand based on the first motion data and second motion data; calculate a left hand motor skill metric as an average amount of time the user moves between the updating and the receiving when the instructions specify that the left hand must be used; and calculating a right hand motor skill metric as an average amount of time the user moves between the updating and the receiving when the instructions specify that the right hand must be used.

In some disclosed embodiments, the user may follow instructions to perform a complex reaction test. The instructions may include selecting a first button when the letter A appears on the touchscreen, and selecting a second button when the letter B appears on the touchscreen. The system may provide an interface with the first button and the second button. Additionally, the system may randomly select the letter A or the letter B, and update the graphical user interface to provide the randomly selected letter. The system may determine if the user selected the correct button corresponding to the randomly selected letter. Furthermore, the system may also calculate an average correct response time as the average of time periods where the user selected the correct button corresponding to the displayed letter, and calculate an average incorrect response time as the average, multiplied by a penalty factor of time periods where the user did not select the correct button. The system may further calculate the cognitive ability metric as an average of the average correct response time and the average incorrect response time.

In some disclosed embodiments, the user may follow instructions to perform a different complex reaction test. The instructions may include selecting a button on the left side of the touchscreen if the letter A appears on the left side of the screen and selecting a button on the right side of the touchscreen if the letter A appears on the right side of the touchscreen. The system may randomly select the left side or the right side and update the graphical user interface to show the letter A on the selected side and the letter B on the non-selected side. The system may determine if the user selected the correct button corresponding to the side of the screen containing the letter A. The system may also calculate an average correct response time as the average of time periods in which the user selected the correct button corresponding to the side of the touchscreen displaying the letter A, and calculate an average incorrect response time as the average, multiplied by a penalty factor, of time periods in which the user did not select the correct button. The system may further calculate the cognitive ability metric as an average of the average correct response time and the average incorrect response time.

Still further, in some disclosed embodiments, the user may follow instructions to perform a decision reaction test. The instructions may include selecting a button if the letter A appears and doing nothing if the letter B appears. The system may randomly select the letter A or the letter B and display the selected letter. The system may calculate the user's cognitive ability metric based on the time between when the interface shows the letter A and when the user selects the button. Furthermore, the system may again update the graphical user interface if a time limit, such as three seconds, expires and the user did not select the button.

In another disclosed embodiment, the user may follow instructions to perform a different decision reaction test. The instructions may include selecting a button if there are more As than Bs displayed, and not selecting the button if there are more Bs than As. The system may randomly select the number of As and Bs to display, such as 2 As and 1 B, and display the As and Bs on the touchscreen. The system may update the graphical user interface again if a time limit expires without the user selecting the button. In some embodiments, the system may display a test complete message so that the user and a healthcare professional may know when the user has done the predefined number of trials using the interface. Alternatively, the system may display a test incomplete screen having a save button that allows a healthcare professional to save the visual acuity metric, motor skill metric, and cognitive ability metric even if the requested number of iterations is not complete.

In some disclosed embodiments, the system may calculate a total score reflecting the user's health status. The system may calculate an average of the time data, reflecting how quickly the user responded to updated interfaces, and a correct selection rate as a ratio of a number of correct selections to a number of incorrect selections. The system may also calculate a reaction metric as a quotient of the average time data and the correct selection rate, so that a low correct selection rate raises the reaction metric and a high correct selection rate has a smaller effect on the reaction metric. Further, the system may calculate a number of accelerations recorded in the first motion data that were above an acceleration threshold, such as a number of jitters that occur in the user's hand while moving. The system may also calculate a number of times the user looks way from the screen. The system may sum the reaction metric, the number of accelerations above the threshold, and the number of times the user looks away from the screen, and report the sum as a total score.

Still further, in some disclosed embodiments, the electronic device may have a touchscreen motion sensor, and the user may be given instructions to move the electronic device in some way, such as up, down, or rotation. The system may record the data of the touchscreen motion sensor and determine if the user correctly performed the instructions based on the data. The system may also calculate the motor skill metric based on a number of accelerations measured by the touchscreen motion sensor that exceed an acceleration threshold.

In some disclosed embodiments, the user may follow instructions to touch a physical item, such as the user's nose, before selecting the button on the touchscreen. The system may determine if the user performed the instructions by determining a number of accelerations of the first motion data, reflecting how many times the user started and stopped moving his hand. The system may also calculate the motor skill metric reflecting the shakiness of the user's motion. The system may calculate the motor skill metric based on a number of accelerations above a first threshold (excluding noise) and below a second threshold (excluding large accelerations from gross movement).

Both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
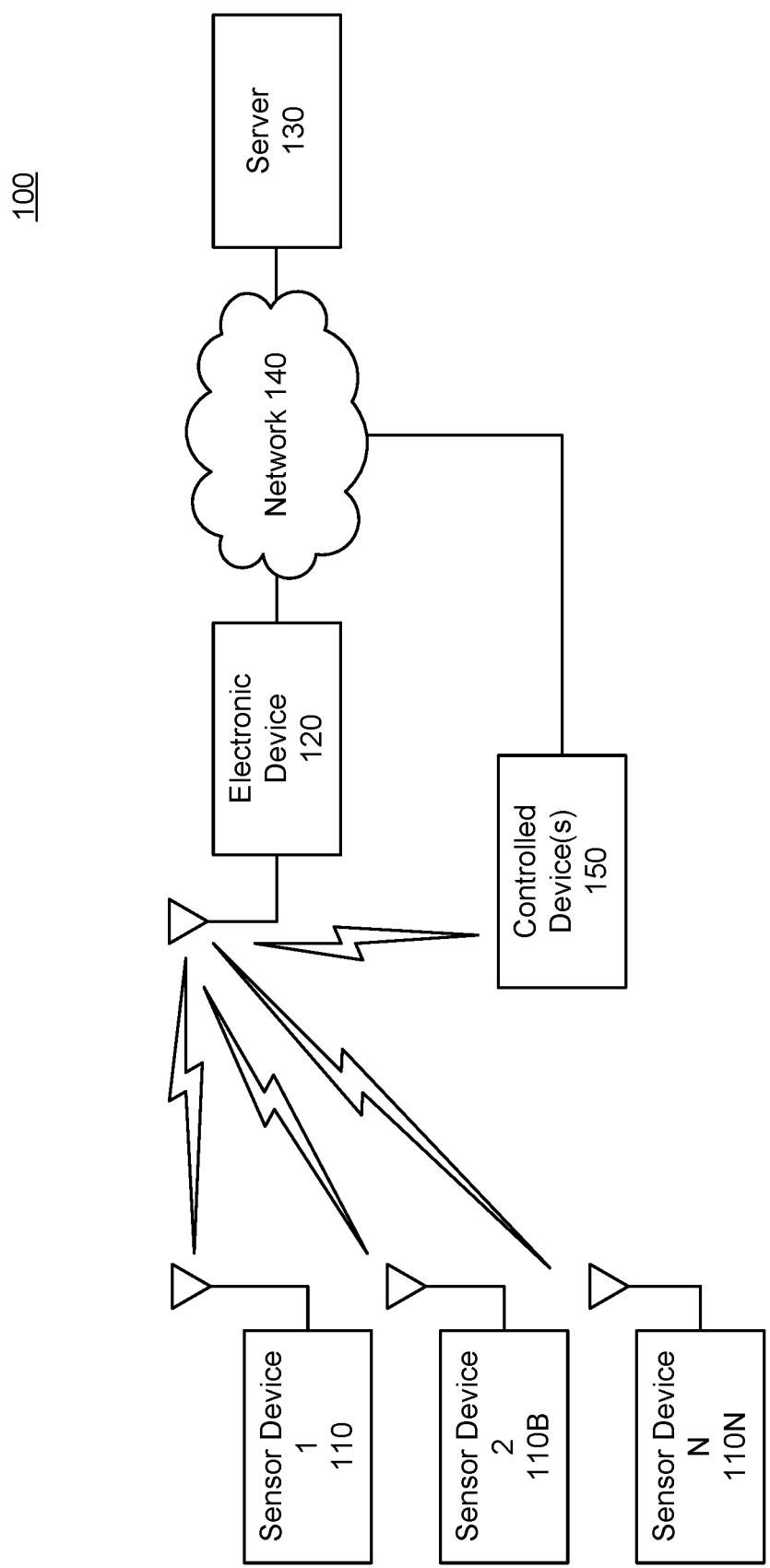
FIG. 1 illustrates an exemplary reaction time measurement, analysis, and feedback system according to some embodiments of the present disclosure.

Exemplary embodiments are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. The following detailed description should be considered as exemplary only, with the true scope and spirit being indicated by the following claims.

Disclosed embodiments generally relate to systems and methods of acquiring data in real-time, analyzing the data, and providing analysis results to a healthcare professional or the user. Disclosed embodiments may track, quantify, and evaluate body motion of a user and/or equipment or machinery. For example, while interacting with an electronic device, user movements may indicate certain medical conditions. Abnormal hand movement when touching a touchscreen, for instance, may reveal limited range of motion for the user. Jittery or shaky movement may also indicate neurological disorders. Comparing a user's movements to typical movements may reveal or quantify these medical issues. Alternatively, comparing a user's movements to the same user's historical movements may help track improvements or degradation of the user's condition.

For example, while the user interacts with the touchscreen, disclosed systems and methods may process motion data quantifying clinically relevant characteristics of hand motions of a user, as well as evaluate the data by comparing it to simultaneously-received data from another user, prior sets of data from the user or other users, and/or model (also referred to as "template") sets of data for a desired motion. For a single test session or for discrete motions performed throughout a session, disclosed systems may provide a quantified measurement of the motion, such as a number of accelerations measured by the sensor device that were above a noise threshold. The number of accelerations may indicate the shakiness, or, in the alternative, smoothness of the motions of the user. Further, over time, disclosed systems may automatically adapt templates or accept manual template changes based on progress from prior measurements and long-term goals. For example, if a user is a physical therapy patient recovering from an injury, templates for user interaction with the touchscreen and surrounding environment may be chosen based on developmental goals. Over time, disclosed systems may allow for cloud-based review of progress by the user or a third party (e.g., a healthcare professional), highlighting problematic results that may benefit from specialized treatment, which may include modifications to exercises or instructive motions, different motion instructions altogether, a varied combination of regimens, medication, and/or surgical treatment.

Existing systems and methods may only track a single metric over time, multiple metrics, or a cumulative metric. Disclosed embodiments may offer the improved functionality of accounting for and correlating different variables associated with an activity. Disclosed embodiments may offer an improved solution by correlating different tracked data over time and recognizing relevant trends or patterns in the data that may not be apparent without multidimensional correlation.

Further, existing systems fail to track changes over time. Disclosed embodiments may offer the improvement of highlighting clinically relevant trends over time between different data profiles. Further, disclosed embodiments may track clinically relevant progress, such as a range of motion or deviation from a template profile. For example, systems and methods may determine that a user experiences pain or reduced range of motion in some activities. For instance, if a user is directed to touch his nose, and does so at a slower speed than expected, the deviation from expectation may indicate painful movement for the user. Alternatively, if the user's arm does not move in a straight path, the user may have limited range of motion in a joint. Furthermore, if the user's hand shakes during the motion, the user may have a neurological disorder. Detecting minute vibrations that the user does not report may help early identification of neurological problems and enable treatment.

While some medical issues may be apparent to the user, exemplary disclosed systems may also uncover latent changes in a user's wellbeing, such as changes in blood-glucose levels, blood pressure, heart rate, oxidation levels, and hydration, for example. Embodiments may correlate such clinically relevant latent characteristics of a user's body with other activities to note trends of problematic activity. Systems and methods may alert the user and/or a healthcare provider. Moreover, insurance providers may use disclosed systems and methods to offer adapted insurance options tailored to an individual, such as decreasing one's rates for maintaining a lower blood pressure through proper medication, diet, and exercise, or advocating for surgical intervention prior to complete failure of some physiological aspect that would otherwise hamper recovery.

Furthermore, disclosed embodiments may provide methods to uncover false claims of pain, sickness, or injury. For example, if a user complains of persistent shakes or limited range of motion, and yet performs motions similar to a standard, a medical professional may be able to determine that the user's issues are not truly present and treat the user accordingly.

Disclosed embodiments may improve on existing systems by adapting goals, such as to reach a desired outcome and/or based on current results. For example, a user's progress may increase or decrease based on environmental factors and the user's unique physiology. When user performance exceeds planned or expected progress, disclosed embodiments may adapt templates to be more aggressive (e.g., higher range of motion, faster, stronger, longer distances, more repetitions, tighter tolerances to a template). However, if a user's progress stagnates or declines, disclosed embodiments may allow for a more relaxed adaptation of a user's template.

Additionally, disclosed embodiments may improve on existing systems by allowing an assessment of visual acuity, cognitive ability, and motor skills simultaneously. Current methods require separate tests for each assessment. In some cases, each assessment must be performed by different personnel, increasing costs, time, and user inconvenience. However, disclosed embodiments can assess all three in the same test. Furthermore, existing systems sometime require the user performing multiple activities, each having different and potentially complicated instructions. In contrast, disclosed embodiments allow testing with simple methods and instructions. In this way, the disclosed embodiments may permit testing of individuals with severe developmental disabilities or language barriers, for whom complicated instructions would be an impediment to quality assessment of health indicators.

Disclosed embodiments may provide one or more of these improvements. Additional improvements may be present in the embodiments but not explicitly listed here. Further, embodiments need not meet one or more of these outlined benefits to necessarily provide advancement over current technology. Additional advancements are discussed throughout this disclosure.

Disclosed embodiments may include generating, utilizing, and/or manipulating a data profile. In some embodiments, a data profile may be a multidimensional data stream over time or a portfolio of multiple time-synchronized streams of data. A data profile may correlate two or more time-dependent sets of data, such as data received from various sensors. For example, a data profile may represent acceleration in three axes over time, or angular velocity in three axes over time. In another example, a data profile may include an accumulated magnitude of movement (e.g., an activity measurement metric) and a recorded blood glucose level over time, or a heartrate, blood pressure, muscle operation, and an activity measurement metric over time. For instance, muscle operation may be measured by strain gauges placed in a band that secures the sensor device to a user's hand so that user movements stretch or contract a strain gauge. In this example, the strain gauge displacement may be converted into a force. In still further examples, data from electromyography (EMG) sensors, temperature sensors, elevation sensors, light intensity sensors, pressure sensors, force sensors, and electrical sensors may be correlated with health information, such as blood-glucose levels, heartrate, blood pressure, oxygen saturation levels, body temperature, respiratory rate, and/or gait. Other types of data streams may be generated using the sensors and types of data discussed in this specification, consistent with disclosed embodiments. Correlations of performance or health related to elevation, light intensity, temperature, humidity or other external factors are expected.

Disclosed embodiments may include generating, utilizing, and/or manipulating a motion profile. A motion profile may be a data profile that describes the motion of an object, person, and/or extremity over time. A motion profile may include a timewise multidimensional record of motion. For example, motion profiles may include three-dimensional acceleration data, three-axis orientation data, three-axis angular velocity data, and/or three-axis gravitational information over time. In some embodiments, the acceleration and/or orientation data may include data for less than three dimensions, such as single or dual axis acceleration and/or orientation data. The motion profile may combine unique signals of the same motion, such as correlating linear acceleration and angular acceleration.

Based on the motion profile, disclosed embodiments may include rendering a graphical representation of a corresponding motion in space. In the example of a three-dimensional motion profile, disclosed embodiments may include rendering a line in a three-axis space illustrating the path of the object. In still further embodiments, the rendered display may include an animation showing an icon oriented (e.g., based on orientation data) and moving along the path at a rate commensurate with the acceleration data of the motion profile. Such data may also be rendered alongside or overlaid on top of synchronized captured video data.

Disclosed embodiments may include comparing two or more motion profiles or, more generally, data profiles. In some embodiments, systems and methods may determine the magnitude of the differences between two profiles. Such differences may indicate how closely two sets of data match. The differences may be quantified using different calculations. In one example, disclosed embodiments may sum the aggregate difference of a fixed period of time (e.g., integrate the differences). Some embodiments may normalize the integrated amount on a per unit time basis. Additionally or alternatively, disclosed embodiments may include comparing two profiles by determining that at a predefined set of points in time (e.g., one or more timewise data points) the two profiles differed by more than a threshold amount (e.g., a predefined threshold or an automatically adjusted threshold). In another example, disclosed embodiments may provide a count of a number of acceleration events that exceed a threshold or fall within a range.

Disclosed embodiments may include utilizing event models to recognize data profiles, motion profiles, or portions of either that match particular criteria. These criteria may include simple thresholds, complex curve-matching algorithms, or machine learning-based algorithms. In the example of complex curve fitting, an event model may be defined by a specified contour for particular variables of a profile, such that the y-axis displacement (e.g., ordinary least squares difference) or orthogonal distance (e.g., total least squares difference) is below a threshold amount. The amount may be normalized based on the type of application or magnitude of the test profile data.

Disclosed embodiments may use one or more of these concepts individually or in combination as discussed below regarding the figures.

FIG. 1 illustrates an exemplary reaction time measurement, analysis, and feedback system 100 according to some embodiments of the present disclosure. System 100 may include one or more sensor devices (110, 110B, 110N), electronic device 120, controlled device(s) 150, network 140, and server 130.

System 100 may include one or more sensor devices to aggregate sensor data. Sensor devices 110, 110B, and 110N represent the one or more sensor devices that provide data to system 100. Each of the shown sensor devices may include the same sensor capabilities or different capabilities. For example, sensor 110 may include an inertial measurement unit, while sensor device 110B provides strain gauge data (e.g., from a strain gauge in a band wrapped around a user's wrist or hand). In a differing example, the entire sensor shown could only include inertial measurement units but could be located on different limbs or on different points of a single limb (e.g., hand, wrist, elbow). Sensors may provide various sensed data to system 100 as further discussed below. Additionally, some embodiments may include multiple types of sensors in a single device, such that a single connection is used to communicate multiple types of data to electronic device 120.

System 100 may include electronic device 120. In some embodiments, electronic device 120 may be a general purpose computer, tablet device, smartphone, or smart watch. Electronic device 120 may include at least one processor, memory (e.g., RAM, flash memory, and/or a hard disc), various wired and wireless interfaces (e.g., Bluetooth, IEEE 802.11, Ethernet, USB, USB-C, and/or proprietary ports such as Apple Lightning), input devices (e.g., touchscreen, keyboard, mouse), and a display. Electronic device 120 may operate programmable instructions stored locally or remotely to perform disclosed processes.

Electronic device 120 may interact with one or more sensor devices. Electronic device 120 may receive sensor data from sensor device 110, sensor device 110B, and/or sensor device 110N. For example, sensor device 110 may send, in real-time, data perceived from sensors. Sensor data may be high-resolution data, and the connection between sensor device 110 and electronic device 120 may be a high-bandwidth connection, such as a Bluetooth "classic" wireless connection. While such high-bandwidth wireless technologies may use more power than alternatives (e.g., Bluetooth "low energy"), the increased data resolution that may be used by system 100 may require higher bandwidth wireless interfaces. Electronic device 120 may also include an internal sensor (not shown) that records similar data as sensor device(s) 110, 110B, and 110N.

System 100 may include controlled device(s) 150 that perform functions based on received instructions. For example, controlled device(s) 150 may include output devices, such as remote displays, speakers, and tactile engines that provide feedback to a user of sensor device 110. These types of controlled devices may provide a status indicator to the user based on the sensor data, such as informing the user that the sensor device is providing a data profile that meets expectations by displaying a green light, playing a positive tone, or tapping the user via a worn tactile engine.

In another example, controlled device(s) 150 may include devices that affect a user's workout environment. For example, controlled device(s) may include a fan, air conditioning system, or workout equipment. In this example, electronic device 120 may transmit instructions to increase a fan speed and/or activate an air conditioner responsive to determining that the sensor device 110 indicates that a user's body temperature exceeds a healthy threshold level.

In still other examples, controlled device(s) 150 may include medical devices, such as insulin pumps, pacemakers, cardiac defibrillators, gastric stimulators, deep brain neurostimulators, and/or cochlear implants. In one example, electronic device 120 may transmit a control signal to an insulin pump to vary insulin dosage based on data from sensor device 110 indicating higher levels of activity (e.g., a data profile matching an event model for intensifying activity). In another example, electronic device 120 may transmit a control signal to a medication pump to provide medication to prevent or greatly lessen Parkinsonian tremors. For example, a medication pump may dispense medication to reduce tremors if a sensor device detects an increase in tremor severity while a user is performing tests.

System 100 may include network 140. In some embodiments, network 140 may be a wired and/or wireless network. For example, network 140 may be a LAN, WAN, WLAN, or the Internet. System 100 may use network 140 to connect various devices. For example, electronic device 120 may connect to server 130, controlled device(s) 150, and/or sensor device 110 using the network. Alternatively, as depicted, electronic device 120 may interface directly with sensor device 110 and/or controlled device(s) 150. For example, electronic device 120 may form its own wireless access point to connect to other devices.

System 100 may include server 130 to provide networked storage and analysis. Server 130 may be a networked computer. Server 130 may include a central processing unit, such as at least one data processor that executes program components for executing user- or system-generated requests. The processor may include specialized processing units or a general purpose microprocessor.

Server 130 may facilitate network-based (e.g., "cloud") storage and data interaction. For example, electronic device 120 may transmit data profiles and the underlying raw data to server 130 for storage. In an embodiment, server 130 may analyze data profiles over time and provide feedback based on changes. Server 130 may transmit notifications (e.g., send email, upload data, revise websites, update databases) based on analysis of data. Alternatively, in some embodiments, computing device may store historical data of metrics for users for baselining and detecting variations in user performance, and server 130 may store duplicate data to protect against inadvertent data loss on electronic device 120.

In some embodiments, server 130 may serve as a portal to allow users to interact with archived data profiles and raw data. For example, server 130 may provide a graphical user interface that presents data profiles organized by particular categories, dates, or types.

Figure 2:
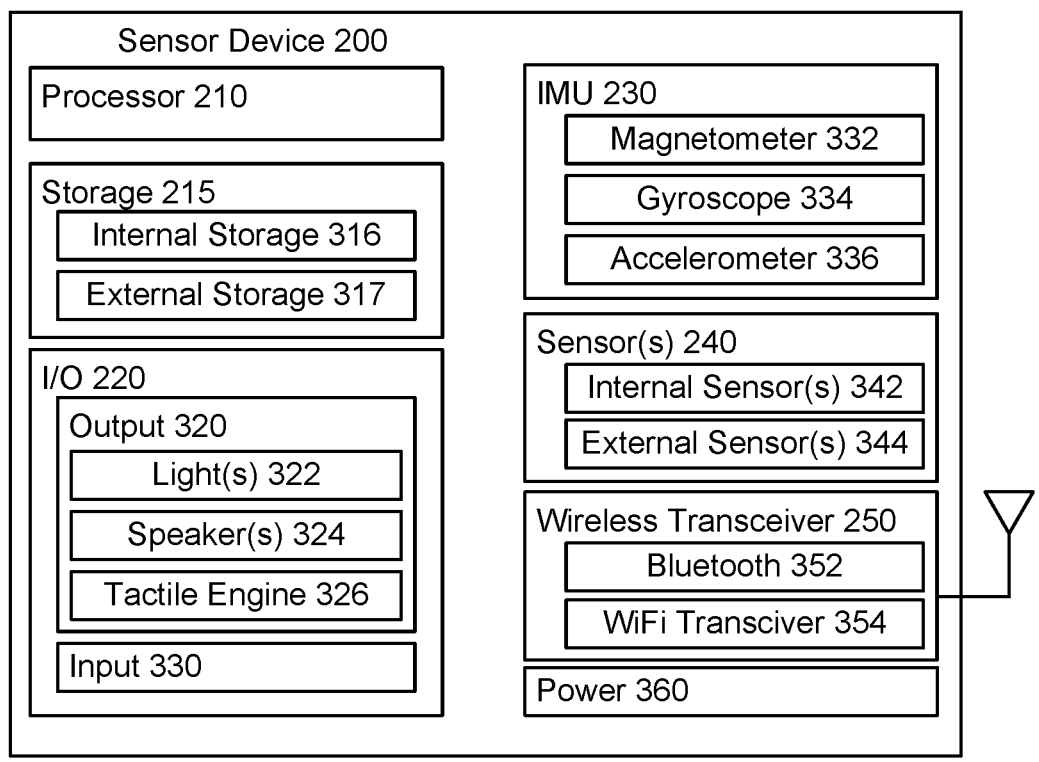
FIG. 2 is a functional block diagram of a sensor device according to some embodiments of the present disclosure.

FIG. 2 is a functional block diagram of sensor device 200 according to some embodiments of the present disclosure. Sensor device 200 may be an example of sensor device 110, consistent with disclosed embodiments. Sensor device 200 may also be an example of electronic device 120. Sensor device 200 may include processor 210, storage 215, input-output 220, IMU 230 (inertial measurement unit), sensor(s) 240, wireless transceiver 250, and/or power 360.

In some embodiments, processor 210 may be a general purpose processor, programmable microcontroller, programmable processor (e.g., a field-programmable gate array (FPGA) or complex programmable logic device (CPLD)), or an application specific integrated circuit (ASIC).

In some embodiments, storage 215 may include internal storage 316 and/or external storage 317. Internal storage 316 may include, for example, on-board memory, such as flash memory or RAM. External storage may include, for example, removable memory media, such as compact flash cards, secure digital cards, memory sticks, optical disks, and the like. In some embodiments, storage 215 may include non-transitory computer-readable media that stores instructions that, when executed by a processor (e.g., processor 210), cause the processor to perform disclosed functions and processes.

Input-output 220 may include output 320 and input 330. In some embodiments, output 320 may include lights 322 (e.g., on or more LEDs, an LCD display, a laser, a projector), speaker(s) 324 (e.g., a piezoelectric speaker, a buzzer, a siren, a loudspeaker), and tactile engine 326 (e.g., vibrators, haptic feedback mechanisms). Lights 322 may include lights on various surfaces and different angles of sensor device 200.

Input 330 may allow a user to activate and interact with sensor device 200. In some embodiments, input 330 may include a physical input mechanism (e.g., button, switch, capacitive interface) or a way to receive input (e.g., an infrared receiver, an optical receiver, a USB or serial port).

Physical input mechanisms, for example, may allow the user to turn sensor device 200 on and off, synchronize with a computing device, and/or change modes. In some embodiments, input-output 220 may also include a touchscreen that both provides a graphical user interface for outputting data from processor 210 and receives user input by recording locations that a user touches on the screen.

In some embodiments, sensor device 200 may include IMU 230 to capture multi-dimensioned acceleration and orientation data. IMU 230 may include magnetometer 332, gyroscope 334, and/or accelerometer 336. In certain embodiments, processor 210 may sample IMU acceleration and orientation data at a rate of 100 samples per second. In some embodiments multiple IMU devices may be "stacked" and then time sliced to permit N-factor sample rate increases such that two such devices can generate 200 samples per second or even more.

In some embodiments, sensor device may include multiple instances of IMU 230 as a redundant measure to filter outlying measurements. For example, processor 210 may receive three-axis acceleration data from two or more IMUs. Processor 210 may average the acceleration data to increase accuracy, or when there are three or more IMUs, processor 210 may not make use of the highest and lowest readings, averaging the remaining readings to reduce measurement inaccuracies. IMU 230 may include internal noise removal, smoothing, or analog-to-digital conversion to preprocess measured data before providing to processor 210.

Sensor device 200 may also include various sensor(s) 240. In some embodiments, sensors may be embedded in sensor device 200 as internal sensor(s) 342. For example, a temperature sensor, light intensity sensor, humidity sensor, elevation sensor, strain gauge, and/or microphone may be housed within sensor device 200 and may interface directly with processor 210. In some embodiments, sensors may interface with sensor device 200 through a port or physical interface as external sensor(s) 344. For example, through a USB or serial connection, sensor device 200 may receive data from off-board sensors, such as biopotential telemetry measurement devices (e.g., electrocardiogram (ECG), electroencephalogram (EEG), electromyogram (EMG) data), optical input devices (e.g., cameras, rangefinders), and/or smartphone sensors (e.g., smartphone GPS, elevation, time, weather, sound, light). In some embodiments, external sensor(s) 344 may be used to verify data from internal sensor(s) 342.

Sensor device 200 may include wireless transceiver 250. Transceiver 250 may facilitate communication with electronic device 120, network 140, and/or controlled device(s) 150. In some embodiments, transceiver 250 may include Bluetooth transceiver 352 and/or Wi-Fi transceiver 354. In an example, Bluetooth transceiver 352 may be a Bluetooth "classic" transceiver, rather than a Bluetooth "low energy" transceiver in order to provide increased bandwidth to transmit high resolution sensor data (e.g., to electronic device 120) in real-time. In another example, Wi-Fi transceiver 354 may be an IEEE 802.11a/b/g/n/x transceiver. Additional wired and/or wireless standards may be used consistent with the bandwidth requirements of the disclosed systems and processes.

Sensor device 200 may include power 360 to provide electricity to components, such as processor 210 and storage 215, among other elements. In some embodiments, power 360 may include a direct current power source, such as a battery. For example, power 360 may include a lithium ion polymer (LiPo) battery, nickel-metal hydride (NiMH) battery, and/or a nickel-cadmium battery. When power 360 includes a battery, power 360 may further include recharging circuitry, such as an electrical port, a removable battery, and/or inductive charging circuitry.

Figure 3:
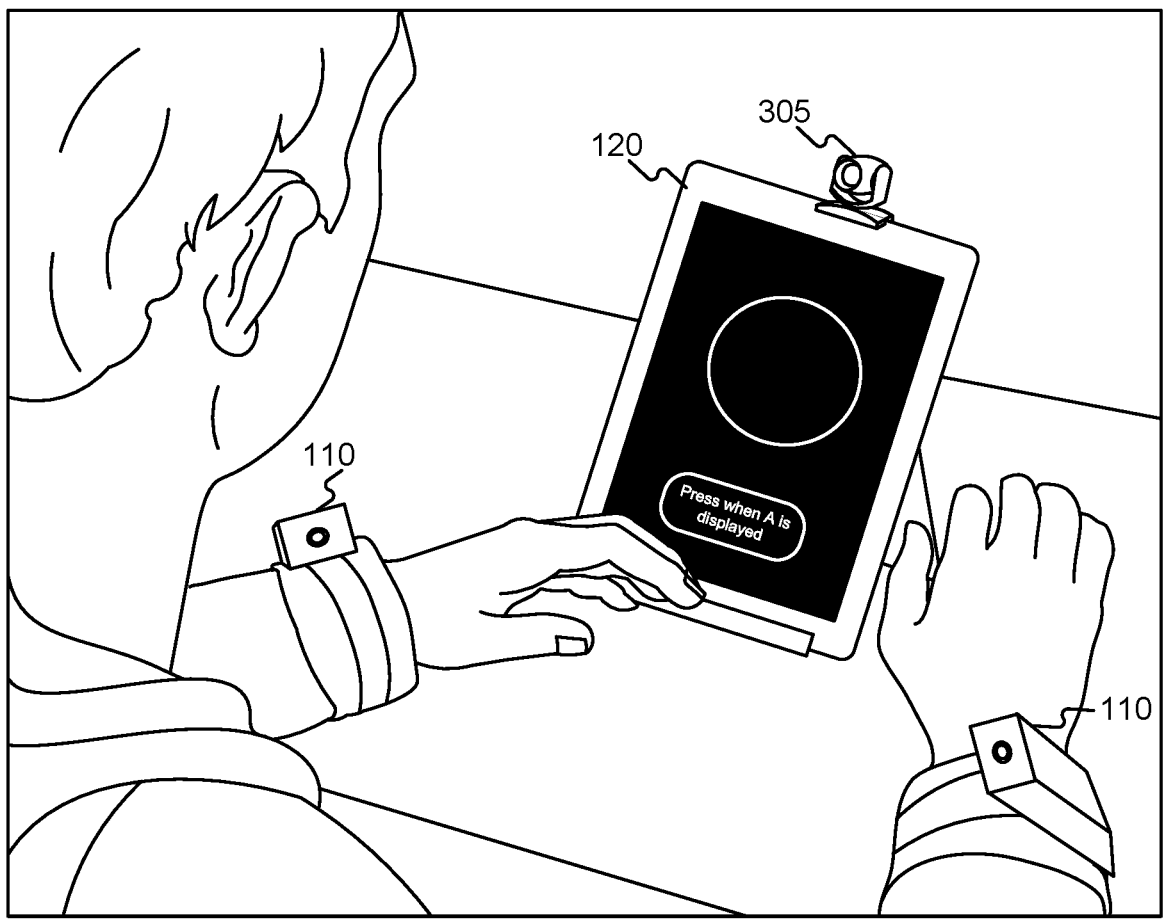
FIG. 3 illustrates a user interacting with an electronic device while wearing sensor devices and performing instructions according to some embodiments of the present disclosure.

FIG. 3 illustrates a user interacting with an electronic device while wearing sensor devices and performing instructions according to some embodiments of the present disclosure. For example, the user may wear a sensor device 110 on both wrists. In some embodiments, sensor devices 110 may be attached to the user by, for instance, a band having hook and loop fasteners. The user may interact with an electronic device 120. Electronic device 120 may be a tablet, or, in some embodiments, a personal computer such as a laptop or desktop computer. Electronic device 120 is connected to a camera 305. As illustrated in FIG. 3, camera 305 may be a peripheral device mounted on electronic device 120 and connected, either wirelessly or physically (e.g., by a pin or wired connection). Alternatively, electronic device 120 may include a camera facing the user, for instance, with the camera lens disposed in the bezel of electronic device 120 and controlled by electronic device 120. In some embodiments, camera 305 may include an internal processor and memory that aid in focusing the lens of the camera independent of instructions from a processor of electronic device 120.

Electronic device 120 may also include a touchscreen that displays a graphical user interface. The graphical user interface may display objects and text that prompt the user to select various fields on the graphical user interface according to the displayed object(s). As the user interacts with electronic device 120, camera 305 remains facing the user and records the user's face. Images recorded by camera 35 are provided to electronic device 120 for processing. Additionally, data, such as accelerations, direction, and displacement, are provided from sensor devices 110 to electronic device 120. Data may be provided wirelessly, or, in some embodiments, a wire may connect sensor devices 110 to electronic device 120. Electronic device 120 may be self-supporting, as illustrated in FIG. 3. Alternatively, the user may hold electronic device 120, allowing the user to move electronic device 120 according to any instructions provided to the user.

While not shown in FIG. 3, sensor devices 110 may be attached to other locations on the user (e.g., head, legs, feet), equipment, such as apparel (e.g., belts, bracelets, shirts, shoes), walking assistance devices (e.g., canes, walkers, scooters, crutches), prosthetics (e.g., hand, arm, leg prosthetics), tools (e.g., hammer, spatula, scalpel), and/or fitness equipment (e.g., medicine balls, jump ropes, helmets, elastic bands).

Figure 4:
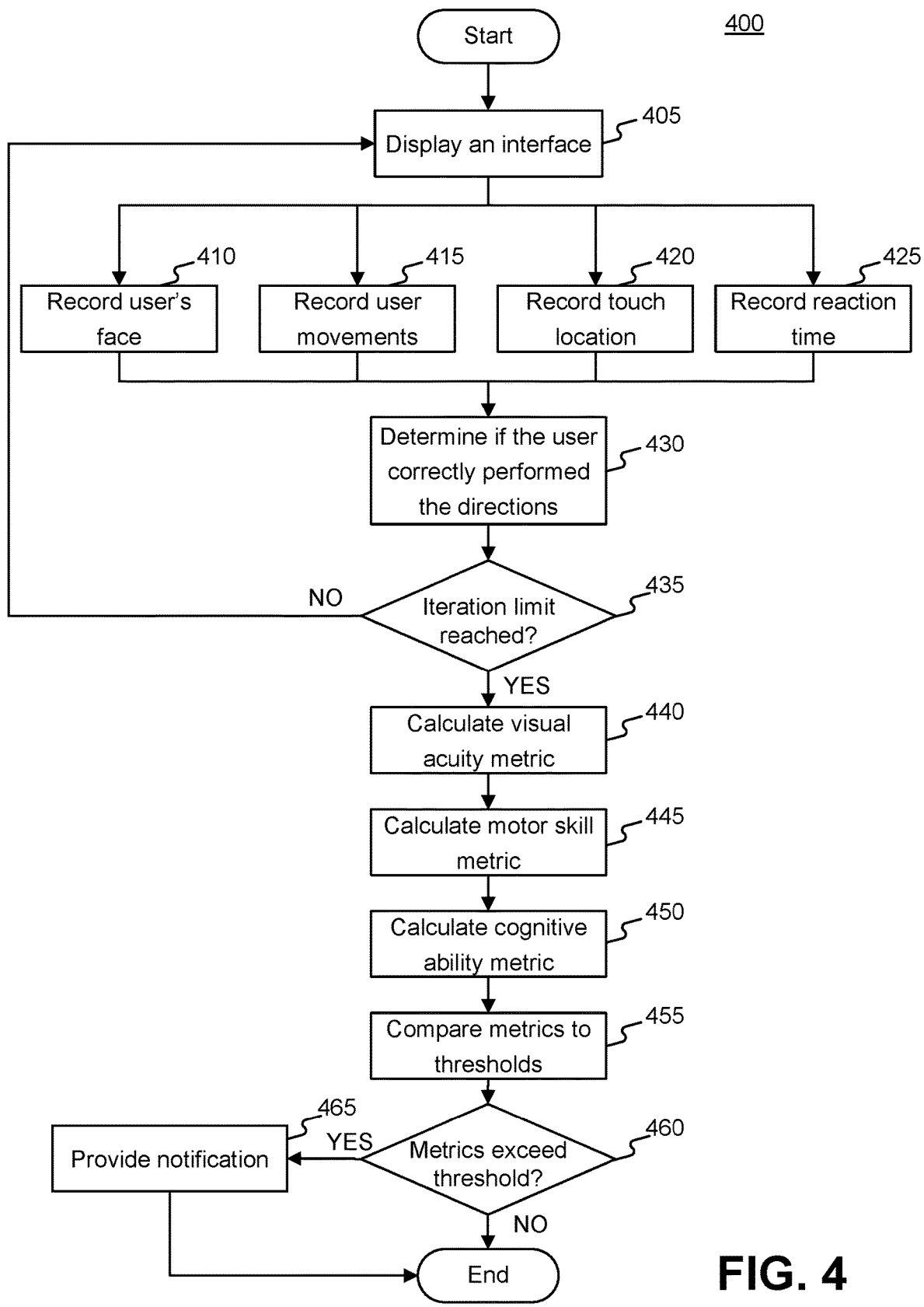
FIG. 4 is a flow diagram illustrating a reaction time measurement and analysis process according to some embodiments of the present disclosure.

FIG. 4 is a flow diagram illustrating a reaction time measurement and analysis process in accordance with some embodiments of the present disclosure. Steps in the following discussion may be described with regard to the actions performed by electronic device 120. However, one or more alternative devices may instead perform the disclosed functions. For example, in an embodiment, sensor device 110 may perform certain data aggregation, calculation, and/or feedback functions locally (e.g., step 415). Additionally, while the steps of process 400 are shown in a particular order, the individual steps may be reordered or omitted.

In step 405, process 400 displays an interface. The interface may be a graphical user interface displayed on a touchscreen of an electronic device, such as electronic device 120. The graphical user interface may test a user's reaction time, vision, and motion. For example, process 400 may provide, on the touchscreen of electronic device 120, a graphical user interface with at least one user-selectable selection region. Furthermore, process 400 may update, at an interval, the graphical user interface to provide at least one object related to a user-selectable selection region. The graphical user interface may display objects and user-selectable fields such as buttons, and electronic device 120 may receive a user selection on the graphical user interface of the touchscreen. For example, the user may be asked to select a button corresponding to characteristics of the objects shown, such as selecting a button on the touchscreen as soon as the letter A is displayed. Additional examples will be provided subsequently by reference to FIGS. 5 and 7-10. The graphical user interface showing a test screen may be displayed multiple times (e.g., refreshed) to provide the user with multiple test screens, allowing the collection of multiple data sets.

The interface may also be a graphical user interface including instructions for the user, objects to which the user responds, and fields or buttons which the user may select in order to follow the instructions. In some embodiments, the instructions may be provided aurally or textually by a healthcare professional rather than being displayed as part of the interface. Additionally, step 405 may occur multiple times to provide multiple interfaces including different information, such as menus and instructions for the user or healthcare professional prior to the start of a test session.

For example, in some embodiments, step 405 may include a calibration procedure. Sensor device 110 may calibrate sensors, such as IMU 230, prior to pairing with electronic device 120. For example, sensor device 110 may provide an indication to a user (e.g., a flashing light of lights 322) to indicate to a user to rotate sensor device 110 so that IMU 230 may align its axes and adjust scaling factors to increase accuracy in position and orientation calculations. In other embodiments, calibration may occur during or after pairing, such as when system 100 determines that the data from IMU 230 lacks necessary precision.

In step 410, process 410 records the user's face. For example, the user-facing camera may record image data including at least a portion of a face of the user. The recorded images may be a video, or a series of still images. Step 410 may also include image processing to smooth, sharpen, color correct, or otherwise improve the image quality for analysis. A camera may record and store the user's face, or may provide live recording to electronic device 120 for processing.

In step 415, process 415 records user movements. First motion data, representing first motions of the user, may be recorded from the first sensor device. User movements may be measured and quantified by sensor devices or a motion sensor in electronic device 120, such as a tablet motion sensor. The user movements may be recorded as accelerations, rotations, or displacements. In this way, step 415 may also include a subprocess to transform raw measurements from IMU 230 such as voltages or resistance from electronic components into representations of physical acceleration, rotations, or displacement.

In step 420, process 400 records a location of where the user touches the touchscreen. In other words, process 400 records location data, from the touchscreen, representing a location of the user selection within the graphical user interface. The touch location may be, for instance, x and y coordinates of the touchscreen. The touch location may be recorded by electronic device 120.

Electronic device 120 may also include an internal clock measuring the time at step 425. Electronic device 120 may record time data, indicating a time period between the updating and the receiving. For example, electronic device 120 may start a timer from the end of step 405 to when the user makes a selection on the touchscreen. The time may be measured in milliseconds. In some embodiments, the time period may end when the user makes a correct selection. Alternatively, if the user follows instructions to not select a button, the time period may be between the updating and an expiration duration of the test screen.

Steps 410, 415, 420, and 425 may be initiated and halted by electronic device 120. For example, process 400 may record data between updating the graphical user interface and receiving a user selection. Data recorded in steps 410, 415, 420, and 425 may be measured by peripheral devices, such as the sensor devices and camera, and provided to electronic device 120 for processing. The data may be measured in raw form, processed by peripheral devices, and converted to be transmitted to electronic device 120 and interpreted. In some embodiments, the data may be recorded by devices internal to electronic device 120, or by a combination of peripheral devices and internal devices. Furthermore, any of steps 410, 415, 420, and 425 may occur simultaneously, sequentially, or at a time determined by the user's actions. For example, a touch location may be recorded only at the time when the user touches the touchscreen.

Additionally, in steps 410, 415, 420, and 425, process 400 may receive real-time sensor data. Electronic device 120 may receive real-time data from sensor device 110 and camera 305. In some embodiments, electronic device 120 may receive sensor data in real-time over a wireless transmission technology such as Bluetooth or Wi-Fi (e.g., using Bluetooth transceiver 352 and/or Wi-Fi transceiver 354). Electronic device 120 may receive packets of data containing real-time data samples from one or more of internal sensor(s) 341 and/or external sensor(s) 344. For example, electronic device 120 may receive one or more packets containing 1-10 samples of data for a given sensor over an interval of 1-5 milliseconds, with less than a 5 millisecond delay from capture by sensor device 110. The samples may be stored as time-value pairs in an array, such as sensor sample values paired with timestamp values in a list. In some embodiments, electronic device 120 may continue to receive sensor data packets so long as sensor device 110 captures data.

In step 430, process 400 determines, based on the location data, if the user performed instructions including selecting the selection region on the touchscreen when at least one corresponding object appears. In other words, process 400 determines if the user correctly selected a button corresponding to the object displayed. For example, in some embodiments, a correct response may include selecting a button when the touchscreen is updated to show the letter A. Thus, step 430 may include comparing the touch location recorded in step 420 to an area the user is expected to select according to instructions provided to the user. For example, a button the user is directed to select may have a known coordinate range on the touchscreen, such as a range of x and y positions measured in pixels. If the recorded location is in the range of the screen defining the button, the user's selection may be counted as correct. In some embodiments, the user may be directed to not select any buttons on the touchscreen given certain conditions. In this case, a selection recorded having coordinates corresponding to the location of the button may register as an incorrect selection. The expected area may be stored, for instance, in a memory of electronic device 120.

Furthermore, multiple buttons may be present, and the user may be directed to select a specific button corresponding to the observed graphical user interface. For example, the user may be directed to select a button for A when the letter A appears and select a button for B when B appears. In this case, step 430 may determine if the correct button, corresponding to the displayed letter, is selected.

In step 435, process 400 checks if an iteration limit has been reached. The iteration limit (also referred to as repetitions) may be set prior to electronic device 120 displaying test screens by providing a graphical user interface allowing a healthcare professional to input a desired number of iterations, corresponding to the desired number of test screens. Once the iteration limit is reached, step 435 is YES, and process 400 continues to step 440. If the iteration limit has not been reached, step 435 is NO, and process 400 returns to step 405 to display a new test screen.

In some embodiments, process 400 may wait for a predefined period before updating the graphical user interface at step 405. This may allow more accurate measurements of a user's performance by avoiding a user rapidly selecting a button on the touchscreen without responding to provided stimulus. In some embodiments, process 400 may wait for a random period before updating the graphical user interface, wherein the random period is within a predefined range. This may further enable accurate assessments of cognitive ability by avoiding a user rhythmically selecting a field without processing stimulus from the touchscreen. A healthcare professional may set the predefined period or predefined range using a user-entry field provided by electronic device 120, for instance, before the start of a test session. Electronic device 120 may receive the user entry and set the predefined period or predefined range to the user entry.

In step 440, process 400 calculates, based on the image data, a visual acuity metric as an average percent of a field of view of the camera that includes the user's face. For example, if a user's face is small in the field of view of the camera, the user is likely positioning himself far away from the camera to better view the touchscreen. This may indicate that the user has difficulty seeing objects on the touchscreen when the touchscreen is close. Alternatively, if the user's face is large in the field of view of the camera, the user may be close to the camera, indicating that the user has difficulty seeing objects that are far away.

Step 440 may include a process to quantify the fraction of the image that contains the user's face. For example, step 440 may remove background images and count the number of remaining pixels in the image to quantify the fraction of the image containing the user's face. Alternative image processing methods known to those skilled in the art may be used to analyze the images.

Furthermore, the percent of the field of view of the camera may be correlated to traditional measures of visual acuity, such as diopter. Alternatively, the visual acuity metric may be recorded as the percent calculated in step 440, without correlation to other clinical metrics, and be recorded in order to identify trends or deviations from historical average. For instance, if a user's face typically fills 75% of the field of view of the camera, but on one test day instead fills 85% of the field of view, a healthcare professional may identify a potential problem with the user's eyesight in reviewing the test results and refer the user for further evaluation.

In some embodiments, process 400 may update the graphical user interface to display the object in a size and a color that differ from a size and color of the object prior to the update at step 405, and calculate the visual acuity metric based on the size and color of the objects at step 440. For example, electronic device 120 may display the letter A in red on a blue background and in a 12-point font size. The percent of the field of view of the camera containing the user's face may be measured for the 12-point font size. In the next iteration, electronic device 120 may display the letter A in a 10-point font size. This may repeat until the percent of field of view of the camera containing the user's face increases. Step 440 may use the font size at which the percent of the field of view containing the user's face increases to calculate the visual acuity metric, for instance, by assigning a higher weight to measurements taken with small font size than to measurements taken with large font size. In some embodiments, multiple visual acuity metrics may be calculated, each corresponding to one of the font sizes. Furthermore, visual acuity metrics may be calculated for different colors displayed. In this way, a healthcare professional may assess a user's color vision and ability to see small objects simultaneously. Other ways to calculate a visual acuity metric using data generated by this technique may be possible.

In step 445, process 400 calculates a motor skill metric as an average amount of time the user moves between the update of the screen and receiving a response from the user based on the first motion data. For example, if the user takes a relatively short time moving in order to select a button on the touchscreen, the user likely has little difficulty moving, either due to pain, coordination, or lack of motor skills. However, if the user spends a longer time moving, it may indicate that the user has difficulty moving. The average time spent moving may be recorded, and a healthcare professional may analyze trends in the time spent moving to identify progress in a user's motor skill development or recovery. In some embodiments, process 400 may calculate the motor skill metric based on a number of accelerations in the first motion data that exceed an acceleration threshold. The acceleration threshold may be set to reduce counts caused by noise in the IMU of sensor device 110, such as 1 inch/sect. The count of accelerations over a threshold may represent the number of shakes or jitters experienced by the user in selecting a field on the touchscreen. Monitoring this metric over time may enable healthcare professionals to assess improvement or degradation in a user's experience of tremors over time.

In some embodiments, a second sensor device may be attached to the user, the second sensor device comprising an inertial measurement unit, the first sensor device being worn on a first hand of the user and the second sensor device being worn on a second hand of the user. Additionally, the instructions may include specifying which hand the user must use when selecting a selection region. For example, the user may follow instructions to use his left hand to select a button if the letter displayed is A, and his right hand to select a different button if the letter displayed is B. Process 400 may record, between the update of the screen and receiving a response, second motion data from the second sensor device representing a second motion of the user, and determine if the user performed the instructions with the correct hand based on the first motion data and the second motion data. For example, process 400 may determine that the sensor device worn on the user's right hand moved when the letter A was displayed, indicating that the user used his right hand when the instructions specified that he should use his left hand. Furthermore, process 400 may calculate, based on the first motion data, a first hand motor skill metric as an average amount of time the user moves between the update of the screen and receiving a response from the user when the instructions specify that the first hand must be used. Process 400 may also calculate, based on the second motion data, a second hand motor skill metric as an average amount of time the user moves between the update of the screen and receiving a response from the user when the instructions specify that the second hand must be used. In this way, separate motor skill metrics may be calculated for both of the user's hands. This may allow a healthcare professional to see discrepancies in the user's ability to control either side of his body, which could aid in assessing neurological damage after stroke, for instance.

Further, in some embodiments, the motor skill metric may include a measurement of the user's ability to move electronic device 120. Thus, electronic device 120 may include a touchscreen motion sensor that measures movement of electronic device 120. The user may also follow instructions to move electronic device 120. For example, instructions may include picking up electronic device 120 when the letter A appears or rotating electronic device 120 by 90 degrees when the letter B appears. Step 415 may include recording, between the update of the screen and receiving a response, data comprising second motion data, from the touchscreen motion sensor, representing second motions of the user. Step 430 may include determining if the user correctly performed the instructions based on the second motion data, for instance, by comparing a rotation measured by the touchscreen motion sensor to the rotation the user was instructed to perform. Step 445 may then calculate the motor skill metric based on a number of accelerations, measured by the touchscreen motion sensor, that exceed an acceleration threshold. This may provide additional data on the smoothness of the user's movements. For example, if sensor device 110 is worn on the user's wrist, sensor device 110 may not detect jittery movement because the distance from the axis of rotation (i.e., the wrist) is small, making overall displacement small as well. However, if the user holds electronic device 120, distance from the axis of rotation is greater, resulting in a greater displacement that may be more easily measured by the touchscreen motion sensor, thus providing an additional measurement of the user's fluidity of motion as quantified in the motor skill metric.

Additionally, if the user is seated throughout the duration of the test, or only moving to touch the touchscreen, other physical impairment may not be detected by sensor devices 110. For example, a user may experience tremors while walking or standing up that sensor devices 110 would not be able to measure. Tremors may also be experienced in other routine motions that are not performed while using a touchscreen. A user may only move his elbow, wrist, and fingers in order to select items on a touchscreen, and tremors experienced when the user moves his shoulder would not be detected. This may be overcome if the instructions include an instruction that the user must touch a physical item before selecting the selection region. This may force the user to perform movements requiring additional joints or limbs, such as requiring that the user touch his nose or walk across a room to touch an object before selecting a button on the touchscreen. Step 430 may include determining if the user correctly performed the instructions based on the second motion data, for instance, by comparing counting a number of accelerations of the first motion data. That is, if a user follows instructions to touch his nose and then select a button on the touchscreen, sensor device 110 would likely measure a first acceleration to start moving the hand, a second acceleration to stop the hand at the nose, a third acceleration to start the hand moving from the nose to the touchscreen, and a fourth acceleration to stop the hand at the touchscreen. If the first motion data includes fewer than four accelerations, step 430 may determine that the user did not follow the instructions. Template data providing correlations between expected numbers of accelerations and instructions or tests may be recorded in a memory of electronic device 120 for comparison to the first motion data at step 430. Additionally, step 445 may calculate the motor skill metric on the basis of a number of accelerations above a first acceleration threshold and below a second acceleration threshold. The first acceleration threshold may eliminate accelerations due to noise, and the second acceleration threshold may eliminate accelerations due to gross movements necessary to perform the instructions, thus leaving minor, but real, accelerations indicative of tremors or shakiness, which may be recorded to reflect the motor skill of the user.

In step 450, process 400 calculates a cognitive ability metric as an average time period between the update of the screen and receiving a response. The average time period between when the graphical user interface updates with a new test screen and when electronic device 120 receives a selection may measure the user's reaction time and ability to process and respond to stimuli. In some embodiments, process 400 may update the graphical user interface to provide a display corresponding to instructions having a difficulty level, based on a number of objects displayed, that differs from a difficulty level of a previous iteration at step 405. In other words, process 400 may determine that the user is easily performing a test sequence, and automatically increase the difficulty of subsequent test screens by including more objects or more complex instructions. For instance, the first set of tests may include a single letter A and the user follows instructions to select a button when the letter A appears. If the user is able to perform this test with relative ease or quick reaction times, process 400 may display a new set of tests with multiple objects, where the user must follow instructions to select a button corresponding to the letter shown most. For example, the touchscreen may display multiple As and Bs, and the user follows instructions to touch a button corresponding to the letter shown the most on the touchscreen. Additionally, step 450 may calculate the cognitive ability metric based on the difficulty level of each iteration. Reaction times for more complex tests may be weighted differently than reaction times for simple tests in calculating the cognitive ability metric.

In some embodiments, step 450 may calculate the cognitive ability metric based on the amount of time the user spends looking at the screen. This may allow an assessment of attention span, or the ability of the user to remain focused on simple tasks. Alternatively, this may reveal that a user is too focused on small tasks, for example, if the user does not take notice of external stimuli provided by a healthcare professional, such as loud sounds or images in the room where the user is performing testing. If the user does not look away from the screen in response to questions, sounds, touch, or other stimuli, the user may have symptoms of a particular behavioral, neurological, or developmental syndrome, such as Asperger syndrome.

Process 400 may identify locations of the user's pupils in the image data and calculate, based on the user's pupil locations, where the user looks. This may be done, for instance, by determining if both pupils are visible to the camera. If not, the user's face is likely to not be facing the touchscreen, and the user may be looking at something in the surrounding environment instead. Furthermore, process 400 may calculate, based on where the user looks, an amount of time the user spends looking at the touchscreen and calculate the cognitive ability metric based on the amount of time the user spends looking at the touchscreen. For example, step 450 may calculate the cognitive ability metric as the average time period the update of the screen and receiving a response of the user, multiplied by the percent of time the user spends looking at the screen.

The technique of identifying a user's pupils may be complicated by the presence of eyeglasses due to glare on lenses interfering with identification of the pupils. Therefore, process 400 may present a graphical user interface asking if the user is currently wearing eyeglasses and receive a user eyeglasses response. If the user is wearing eyeglasses, process 400 may identify the user's eyeglasses in the image data and calculate, based on the user's eyeglasses location, where the user looks. The cognitive ability metric may then be calculated similarly by measuring the amount of time the user spends looking at the touchscreen.

Furthermore, in steps 440, 445, and 450, the calculated metrics may be stored in a memory of electronic device 120 or in a storage of server 130. In this way, historical values may be recorded for individual users. This may allow tracking of the user's progress over time, thereby allowing healthcare professionals to identify improvement or degradation in a user's condition. In some embodiments, process 400 may also provide a graph or chart illustrating the user's performance over time, with statistics such as the average, maximum, minimum, and standard deviation of historical test sessions for the user.

In step 455, process 400 compares the visual acuity metric, motor skill metric, and cognitive ability metric to a visual acuity threshold, motor skill threshold, and cognitive ability threshold, respectively. In this way, if a healthcare professional reviewing individual test results fails to notice a deviation in one of the metrics, process 400 may ensure that important variations are not inadvertently overlooked. For example, the threshold may be based on objective evidence from empirical studies showing higher risks for patients with cognitive ability metrics falling below a certain number as quantified by process 400. The threshold may also be subjective and may compare the user's most recent metrics to the user's historical values. For example, if the user's visual acuity metric increases 10% from the user's baseline average, the user may be experiencing a stroke.

In some embodiments, process 400 may also calculate a total score reflecting all three metrics. Process 400 may calculate an average of the time data. Process 400 may also calculate, based on the determining, a correct selection rate as a ratio of a number of correct selections to a number of incorrect selections. Additionally, process 400 may calculate a reaction metric as a quotient of the average time data and the correct selection rate, such that the average of the time data increases if the user has a low correct selection rate. Process 400 may calculate a number of accelerations above a threshold based on the first motion data, and a number of times the user looks away from the touchscreen, based on the image data. Process 400 may calculate a total score as a sum of the reaction metric, the number of accelerations above the threshold, and the number of times the user looks away. This metric may be tracked over time to provide a measure of the user's performance that is more holistic than the visual acuity metric, motor skill metric, and cognitive ability metrics taken individually.

After comparing metrics to thresholds, process 400 determines if a metric exceeds a corresponding threshold at step 460. If step 460 is YES, process 400 provides, based on the comparing, an alert when at least one of the visual acuity metric, motor skill metric, or cognitive ability metric exceeds the respective threshold at step 465. For instance, electronic device 120 may provide a new screen detailing test results, send an email or text message, or an indication in a list of users showing the users with alerts, such as by bolding users' names or adding text to a warning field in a spreadsheet. In this way, step 465 may serve to draw the healthcare professional's attention to the potential issue, thus aiding the healthcare professional's identification of a potential degradation in user health. Otherwise, if no metric exceeds its respective threshold, step 460 is NO and process 400 ends.

In some embodiments, electronic device 120 may also store the visual acuity metric, motor skill metric, and cognitive ability metric. These metrics may be stored in a memory associated with electronic device 120, server 130, or a cloud storage connected to network 140. The metrics may be correlated with a date or a test session number, and may be stored in a spreadsheet, SQL database, or other data structure. Furthermore, electronic device 120 may use historical data to set a baseline value of visual acuity, a baseline value of motor skill, and a baseline value of cognitive ability as an average of the stored visual acuity metrics, stored motor skill metrics, and stored cognitive ability metrics, respectively. Baseline values may be determined by statistical methods, such as an average, or by a regression analysis having trend lines that predict future values of metrics. For instance, a user may be expected to improve cognitive ability by 10% every week with continued therapy. The visual acuity threshold, motor skill threshold, and cognitive ability thresholds may be based on respective baseline values. For instance, if the average cognitive ability metric for a user over 10 test sessions is 0.30, the threshold may be 10%, or 0.33, such that if a user's cognitive ability metric for a test session exceeds 0.33, a notification is provided. Alternatively, a threshold may be a 10% reduction for every training session, such that if a first training session has a cognitive ability metric of 0.30, the threshold for the second training session may be 0.27 and a notification provided if the user maintains a cognitive ability metric above 0.27 in the second training session.

Figure 5B:
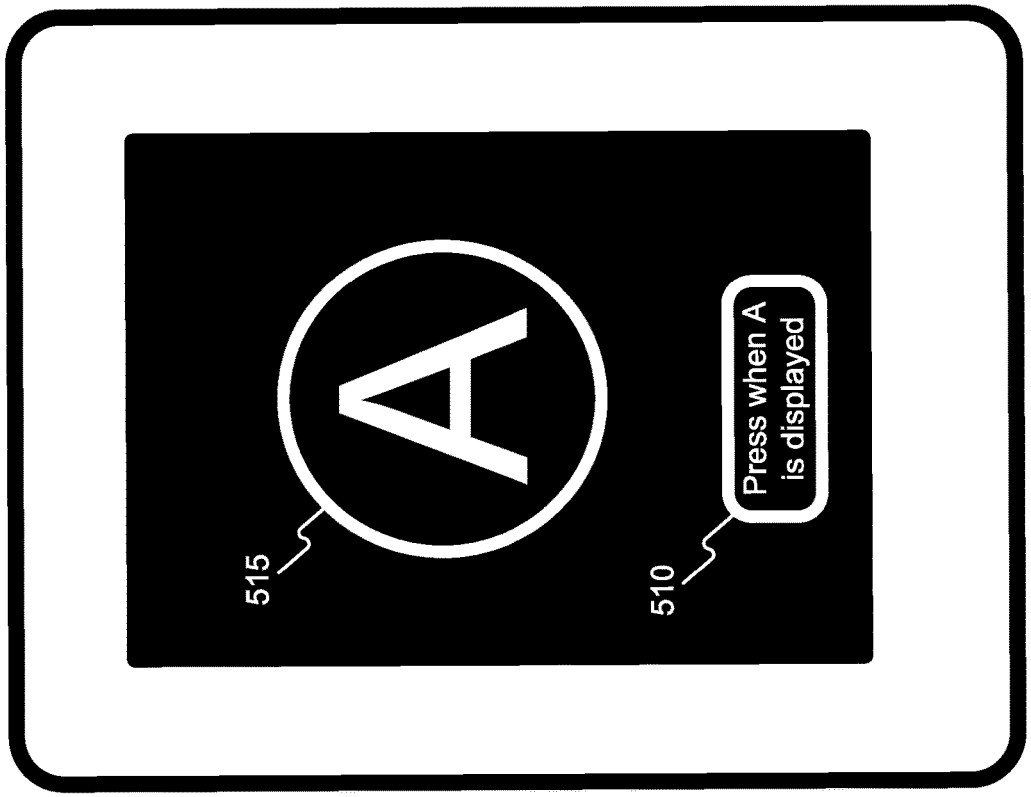
FIGS. 5A and 5B illustrate simple reaction test graphical user interfaces according to some embodiments of the present disclosure.
Figure 5A:
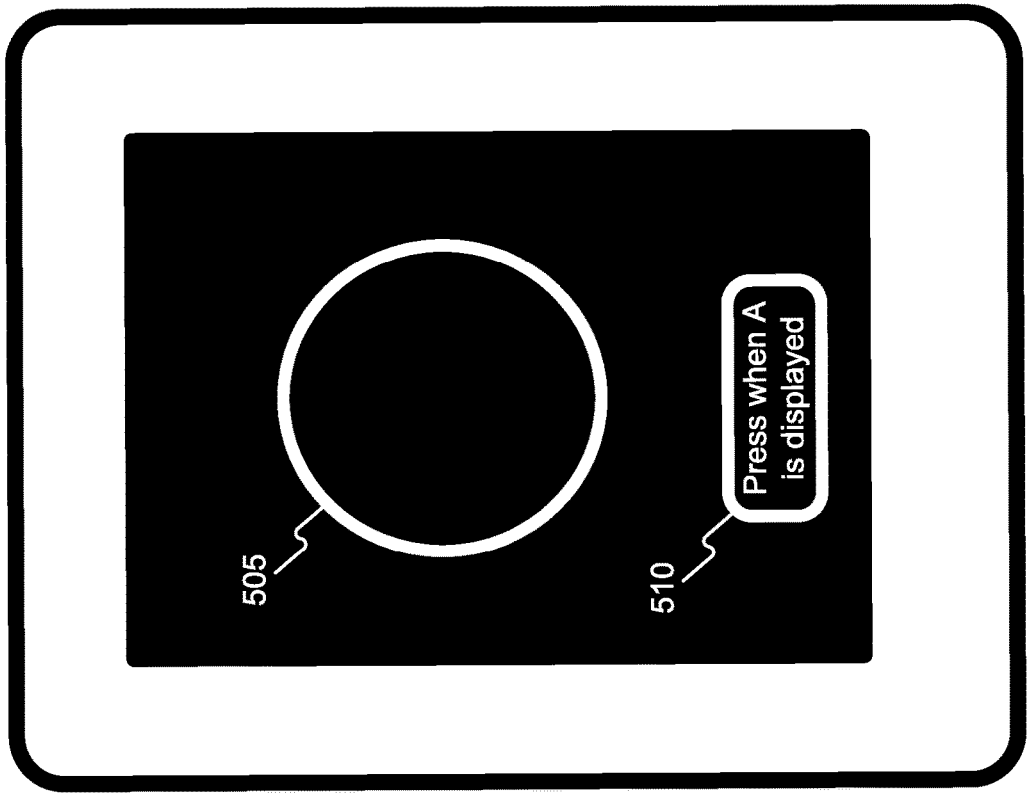

The test screens presented as graphical user interfaces at step 405 of process 400 may be further understood by reference to FIGS. 5A and 5B. FIG. 5A illustrates a first screen 500A and a second screen 500B of a simple reaction test graphical user interface, consistent with disclosed embodiments. First screen 500A may include an empty circle 505 and a button 510 for the user to select when the letter A is displayed. As will be obvious to one skilled in the art, any object may be displayed, and the letter A is used for illustration purposes. At step 405, process 400 may cause the letter A to be displayed in object circle 515, and the user may be instructed to select button 510 as soon as possible after the letter is displayed, as illustrated in second screen 500B. Process 400 may record the user's face, movements, touch location, and time until the user selects button 510 on second screen 500B. In some embodiments, the letter may disappear until a new letter is displayed again at step 405.

Figure 6:
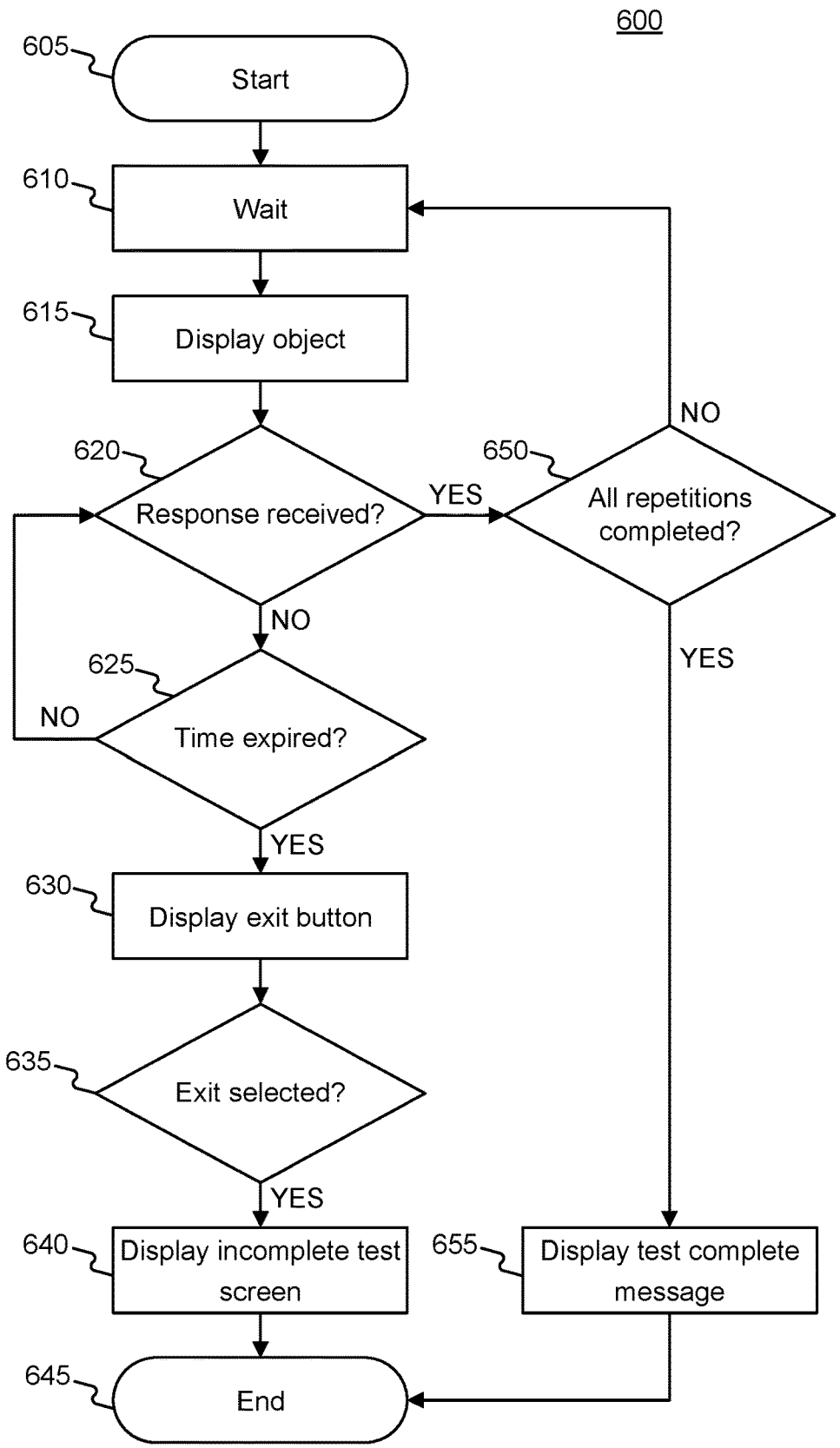
FIG. 6 is a flow diagram illustrating a simple reaction test process according to some embodiments of the present disclosure.

Use of the simple reaction test graphical user interface may be further understood by reference to FIG. 6, illustrating a simple reaction test process 600 according to some embodiments of the present disclosure. In some embodiments, electronic device 120 may perform process 400 and process 600 concurrently.

At step 605, process 600 starts. Process 600 may start upon selection of a start button displayed on the touchscreen. Process 600 then waits for a period of time before proceeding to step 615. As described above, the wait time may be preset or may be of a random duration. At step 615, process 600 displays an object on the screen. The object may be the letter A, and it may be shown in a circle 515 as shown in FIG. 5B. At step 620, process 600 determines if a response was received by the user selecting button 510 on second screen 500B. If no response was received, process 600 proceeds to step 625 and determines if a time limit has expired. If the time limit has not expired, step 625 is NO, and process 600 again checks if a response was received at step 620. If step 625 is YES, process 600 displays an exit button. The time limit may be of a stored duration, such as five seconds, so that the user or healthcare professional may exit the test if desired. Once the exit button is selected, step 635 is YES, and an incomplete test screen is displayed at step 640. The incomplete test screen may include information such as a total test duration, number of tests performed, and metrics calculated on the limited data set. Process 600 may then end at step 645.

Alternatively, if step 620 is YES, such that the user has selected button 510, process 600 proceeds to step 650 and determines if the user has performed all of the repetitions desired. If step 650 is NO, the user must perform more repetitions, and process 600 returns to step 610 to wait and then display an object. If step 650 is YES, process 600 displays a test complete message 655 to confirm that all of the repetitions were completed by the user. The test complete message may include final metrics calculated for the test session. Once the test complete message is displayed, process 600 ends at step 645.

Figure 7B:
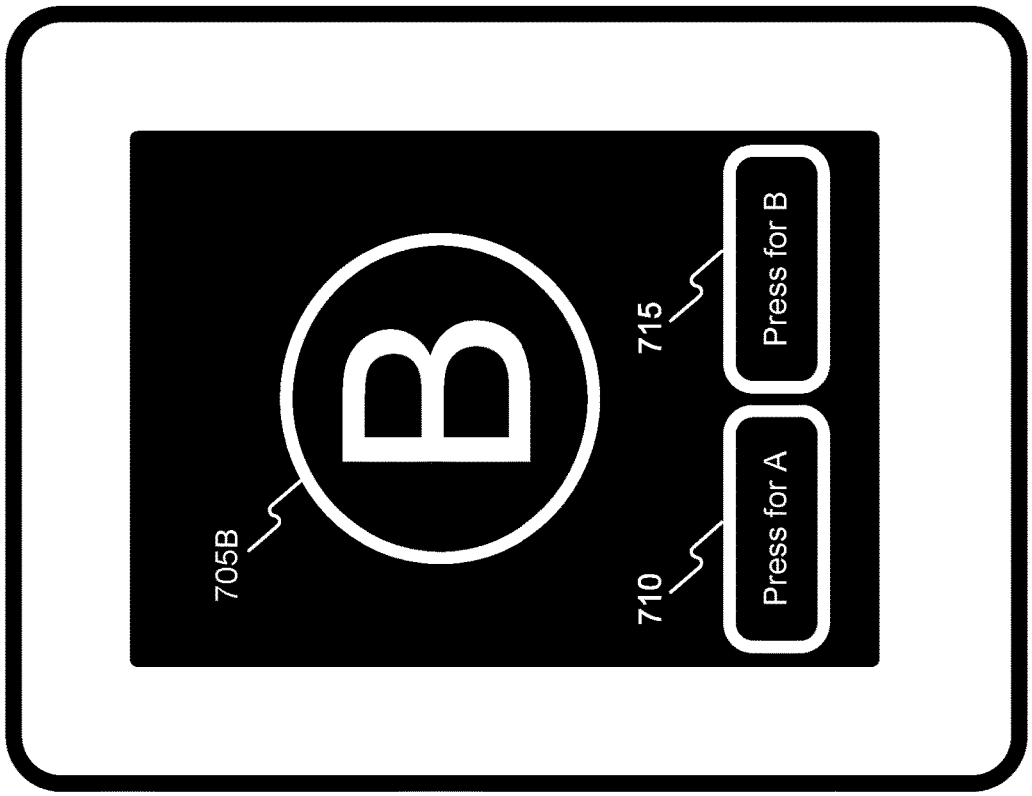
FIGS. 7A and 7B illustrate complex reaction test graphical user interfaces according to some embodiments of the present disclosure.
Figure 7A:
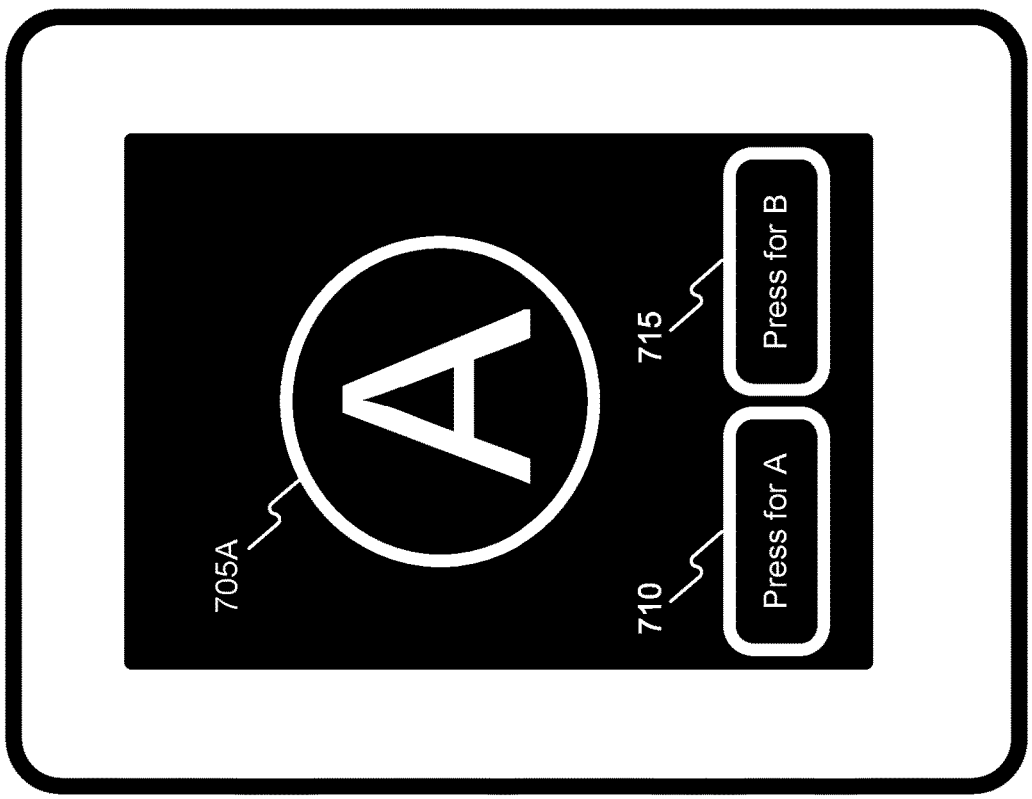

Process 400 may also be used in conjunction with a complex reaction test. The complex reaction test may be further understood by reference to FIG. 7A, illustrating a first screen 700A, and FIG. 7B, illustrating a second screen 700B, of a complex reaction test graphical user interface, consistent with disclosed embodiments. A complex reaction test interface may be presented as graphical user interfaces at step 405 of process 400, such that process 400 provides a graphical user interface with a first selection region and a second selection region.

When conducting the complex reaction test, a user may follow instructions including selecting the first selection region when the first object appears and selecting a second selection region when a second object appears. For example, if the letter A is displayed as shown in the object circle 705A of first screen 700A, the user may be expected to select the A button 710. Alternatively, if the letter B is displayed, as shown in the object circle 705B of second screen 700B, the user may be expected to select the B button 715.

Additionally, process 400 may randomly select the first object or the second object and update the graphical user interface at step 405 to provide the randomly selected object. For instance, a random number generator may be used to select the letter A or the letter B to display on the touchscreen. Step 430 of process 400 may also determine, based on the location data from the touchscreen, if the user selected the selection region corresponding to the randomly selected object (i.e., the A button if the letter A is shown). Step 450 of process 400 may further include calculating an average correct response time as the average of time periods where the user selected the selection region corresponding to the randomly selected object and calculating an average incorrect response time as the average, multiplied by a penalty factor, of time periods where the user did not select the selection region corresponding to the randomly selected object. Step 450 may also calculate the cognitive ability metric as an average of the average correct response time and the average incorrect response time. In this way, a user that selects the wrong button frequently will likely have high average response times and high cognitive ability metric values, even if individual responses occur quickly.

Figure 8B:
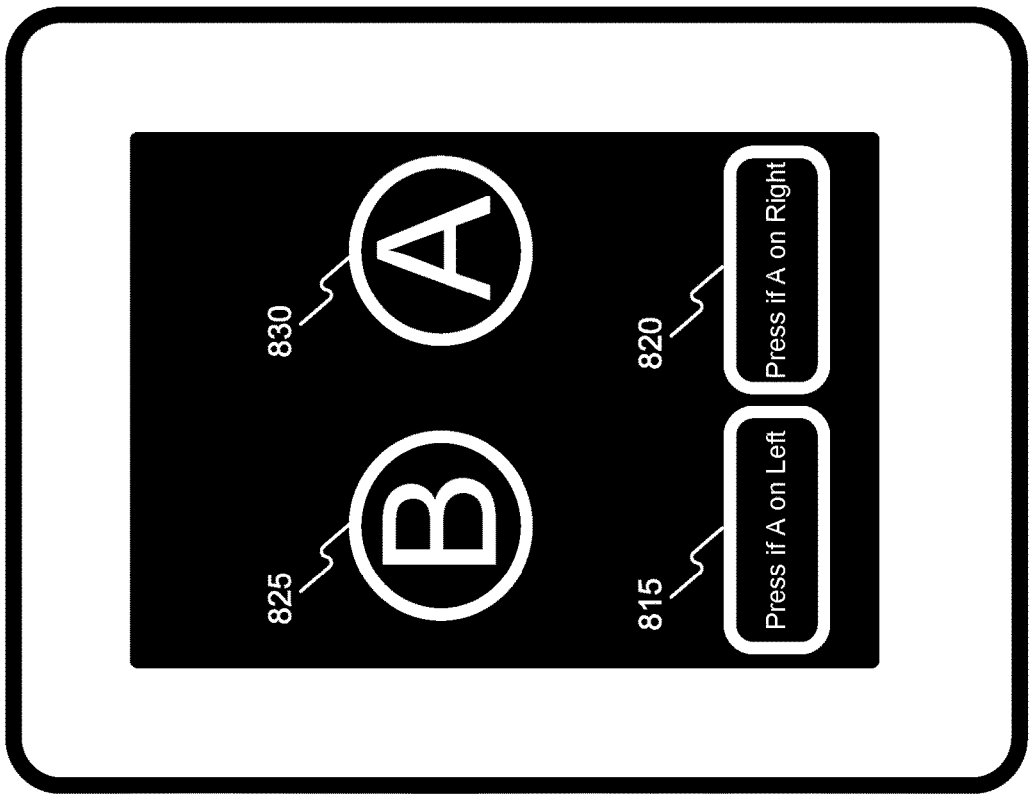
FIGS. 8A and 8B illustrate complex reaction test graphical user interfaces according to some embodiments of the present disclosure.
Figure 8A:
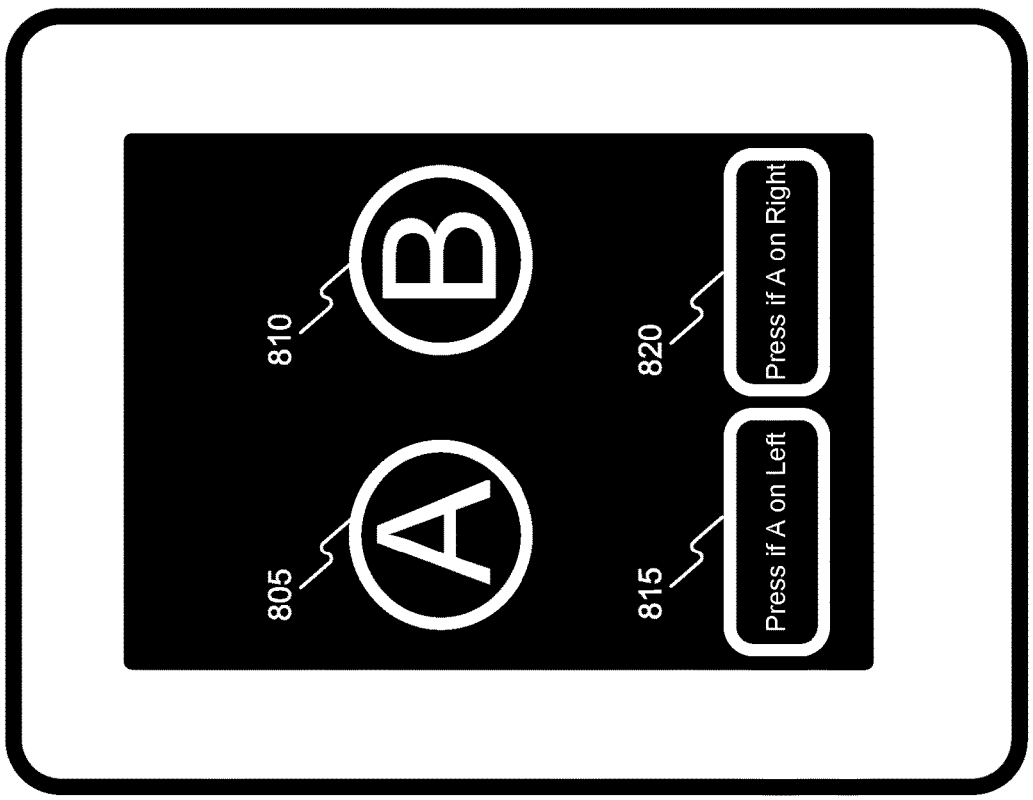

Alternatively, the complex reaction test may be understood by reference to FIGS. 8A and 8B. FIG. 8A illustrates a first screen 800A, and FIG. 8B illustrates a second screen 800B for use in the graphical user interfaces of the complex reaction test, consistent with disclosed embodiments. In this version of the complex reaction test, the user may follow instructions including selecting a first selection region when the first object appears on a first side of the touchscreen and selecting a second selection region when the first object appears on a second side of the touchscreen. Furthermore, process 400 may provide the graphical user interface with the first selection region and the second selection region. For example, as shown in FIGS. 8A and 8B, process 400 may provide a left side button 815 and a right side button 820, and the user may follow instructions to select left side button 815 if the letter A is on the left side of the touchscreen, and select the right side button 820 if the letter A is on the right side of the touchscreen.

Process 400 may also randomly select the first side or the second side of the touchscreen, and, at step 405, update the graphical user interface to provide the first object on the randomly selected side and a second object on a remaining side. For example, the touchscreen may be divided into a left side and a right side. Process 400 may select the left side randomly and display the first object (i.e., the letter A) on the left side of the screen, as shown in object circle 805 of test screen 800A. Process 400 may display the second object (i.e., the letter B) on the right side of the screen as shown in object circle 810 of test screen 800A. Alternatively, if process 400 randomly selects the right side of the screen, the letter A may be shown on the right side in object circle 830 and the letter B shown on the left side in object circle 825. Steps 430 and 450 of process 400 may then proceed to calculate the cognitive ability metric as described above for the first version of the complex reaction test.

Figure 9B:
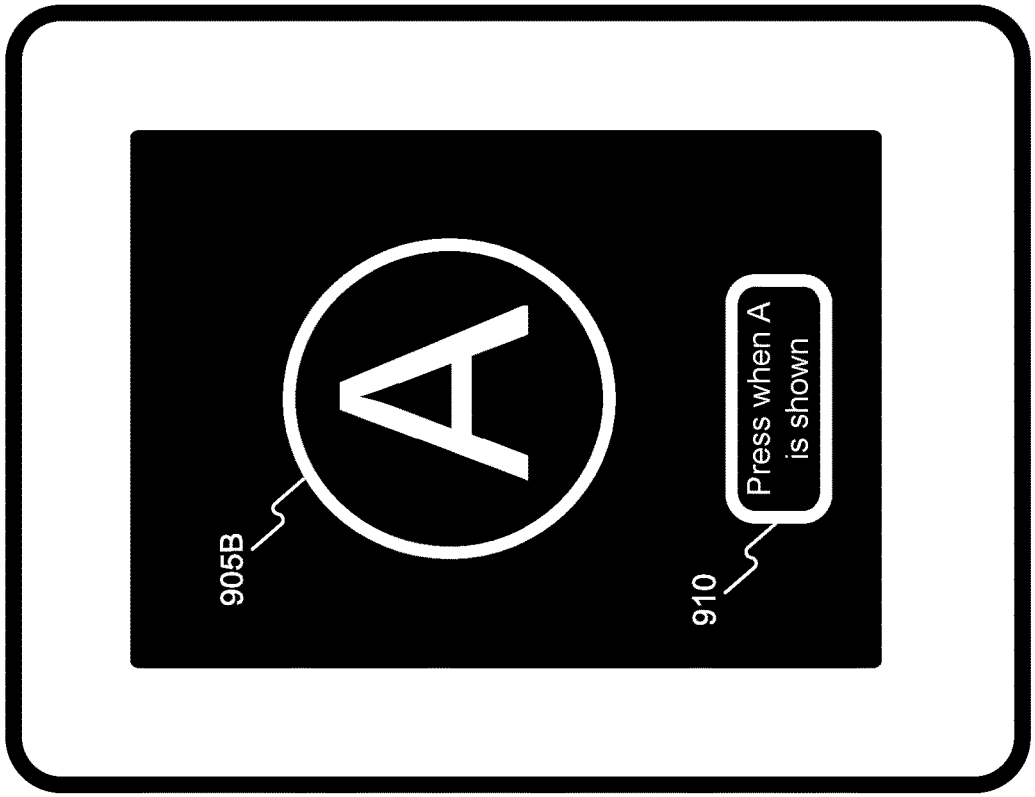
FIGS. 9A and 9B illustrate decision reaction test graphical user interfaces according to some embodiments of the present disclosure.
Figure 9A:
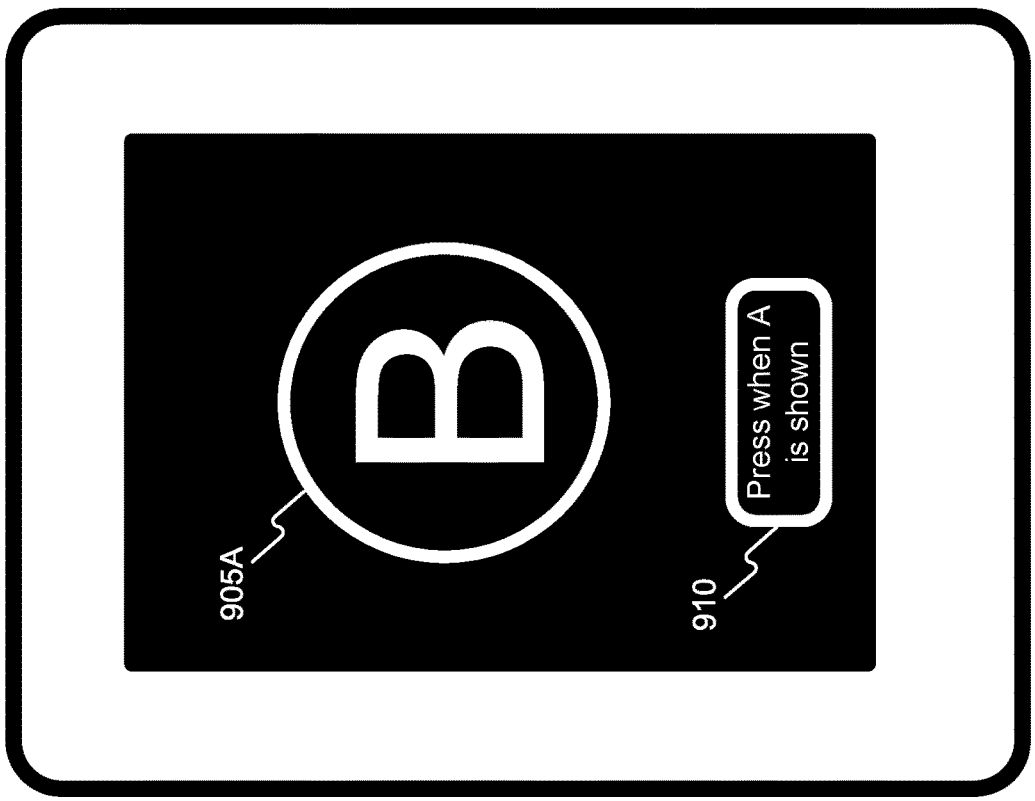

Furthermore, process 400 may be used in conjunction with a decision reaction test. The decision reaction test may be further understood by reference to FIG. 9A, illustrating a first screen 900A, and FIG. 9B, illustrating a second screen 900B, of a decision reaction test graphical user interface, consistent with disclosed embodiments. A decision reaction test interface may be presented as graphical user interfaces at step 405 of process 400, such that process 400 provides a graphical user interface with a selection region (i.e., button 910) as illustrated in FIGS. 9A and 9B.

When conducting the decision reaction test, a user may follow instructions including selecting the selection region when the first object appears and not selecting the selection region when a second object appears. For example, if the letter B is displayed as shown in the object circle 905A of first screen 900A, the user may be expected to not select button 910. Alternatively, if the letter A is displayed, as shown in the object circle 905B of second screen 900B, the user may be expected to select button 910.

When providing the decision reaction test, process 400 may randomly select the first object or the second object, and, at step 405, update the graphical user interface to provide the selected object. For example, process 400 may randomly select and display the letter A in object circle 905. As stated above, if the second object is displayed, the user may follow instructions to not select the selection region. Thus, if a time limit expires and the user did not select the selection region, process 400 may update the graphical user interface. For example, as shown in test screen 900A, the letter B is displayed in object circle 905A. In order to comply with the instructions, the user must not select button 910. In this illustrative example, process 400 may update the screen if a time limit, such as three seconds, expires and the user did not select button 910.

Figure 10B:
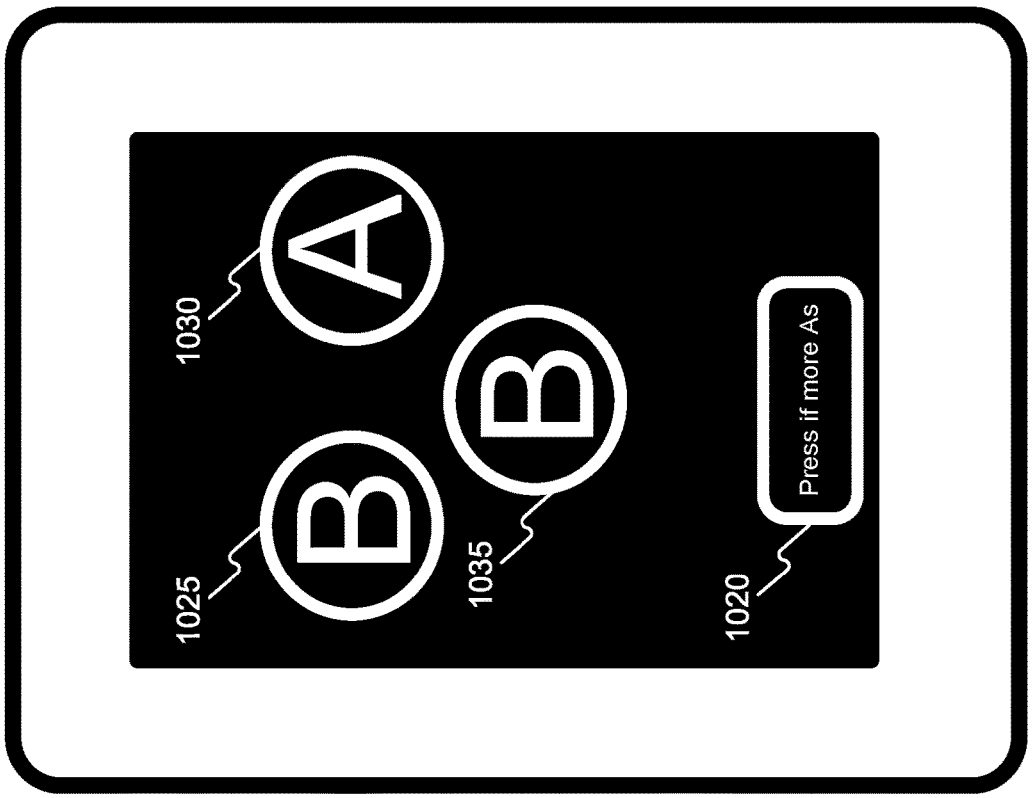
FIGS. 10A and 10B illustrate decision reaction test graphical user interfaces according to some embodiments of the present disclosure.
Figure 10A:
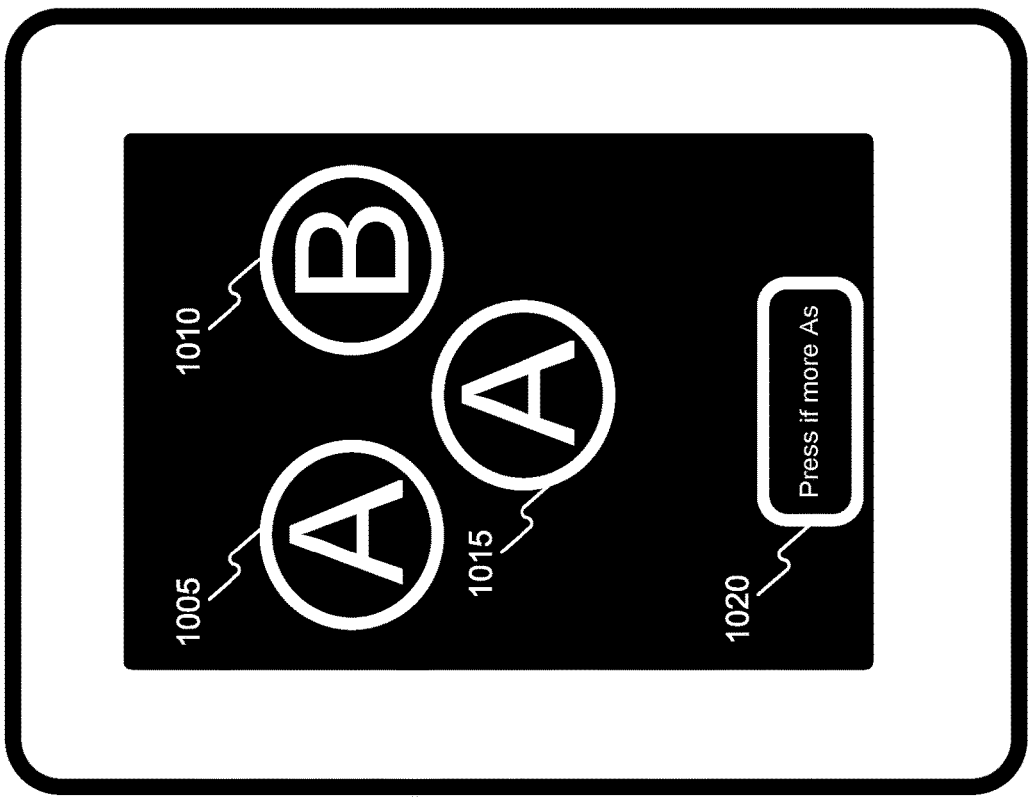

An alternative decision reaction test may be understood by reference to FIGS. 10A and 10B. FIG. 10A illustrates a first screen 1000A, and FIG. 10B illustrates a second screen 1000B for use in the graphical user interfaces of the decision reaction test, consistent with disclosed embodiments. In this version of the decision reaction test, the user may follow instructions including selecting a selection region (i.e., button 1020) when a number of first objects exceeds a number of second objects, and not selecting the selection region when the number of first objects is less than the number of second objects.

For example, as shown in FIGS. 10A and 10B, decision reaction test screens 1000A and 1000B may include a plurality of object circles containing letters. In FIG. 10A, test screen 1000A displays three object circles, 1005, 1010, and 1015, each containing a letter A or B. The user may follow instructions to select button 1020 in test screen 1000A because there are two As and one B. However, in FIG. 10B, test screen 1000B displays more Bs than As in object circles 1025, 1030, and 1035. Thus, the user may follow instructions to not select button 1020 in test screen 1000B.

Process 400 may also randomly select the number of first objects and the number of second objects to display on the interface, and, at step 405, update the graphical user interface to provide the first objects and the second objects. Furthermore, process 400 may update the screen if a time limit, such as three seconds, expires and the user did not select button 1020.

Figure 11:
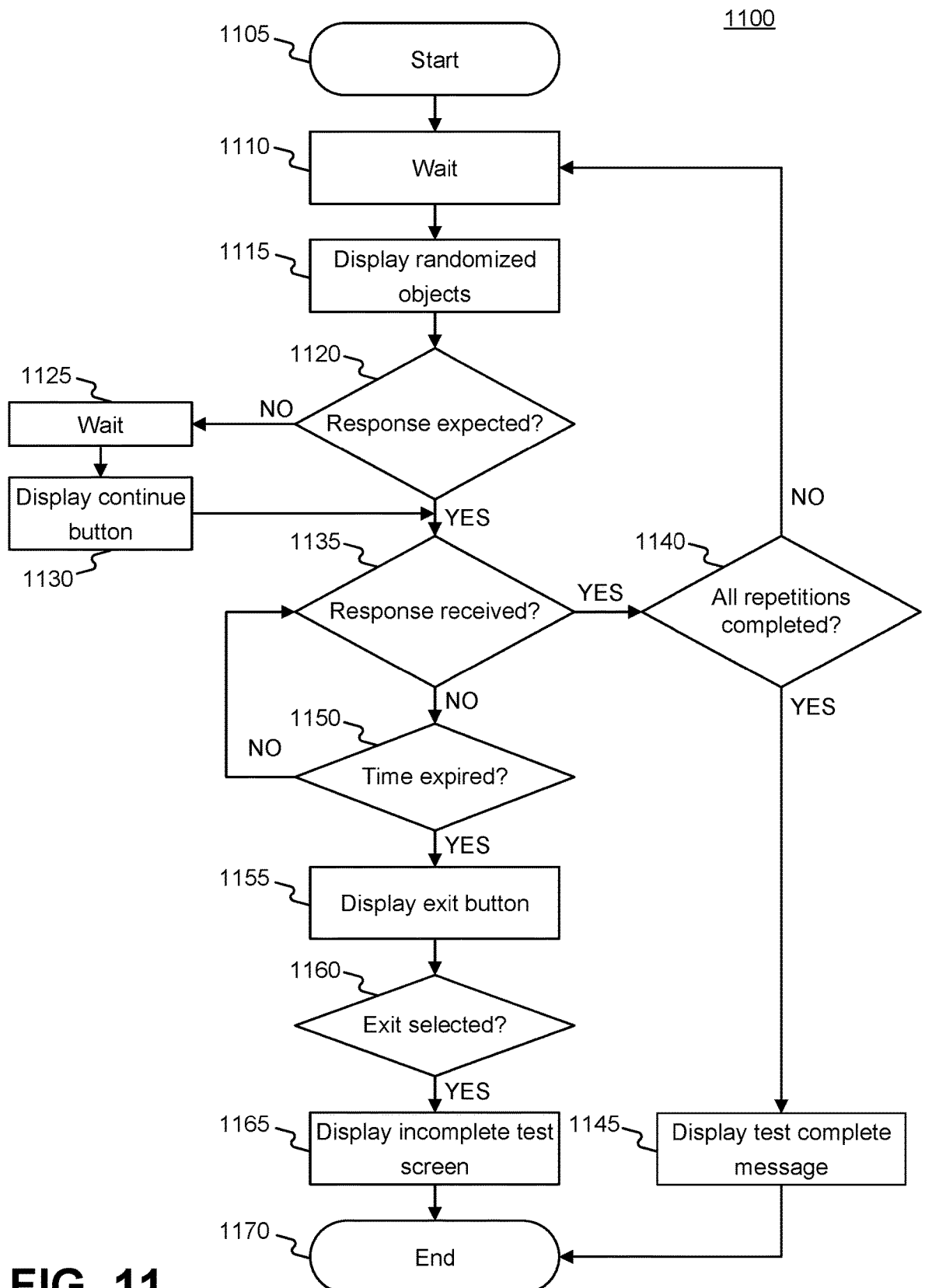
FIG. 11 is a flow diagram illustrating a decision reaction test process according to some embodiments of the present disclosure.

Performance of the decision reaction test may be further understood by reference to FIG. 11, illustrating a decision reaction test process 1100 according to some embodiments of the present disclosure. In some embodiments, electronic device 120 may perform process 400 and process 1100 concurrently.

At step 1105, process 1100 starts. Step 1105 may occur after a user or healthcare professional selects a start field on electronic device 120. At step 1110, process 1100 waits for a period of time that may be preset or randomly determined from a range of times. At step 1115, process 1100 displays randomized objects. The total number of objects, division of the number of objects, types of objects, and locations of objects may all be randomly selected. For example, electronic device 120 may randomly select three objects, two As and a B, to display as shown in FIG. 10A.

As described above, depending on the instructions provided to the user, process 1100 may expect a response at step 1120 based on the objects displayed at step 1115. For instance, if two Bs and an A are displayed and the user follows instructions to select a button if there are more As, process 1100 may not expect a response from the user, and step 1120 is NO. Process 1100 then waits for a period of time, such as three seconds, to ensure that the user has an opportunity to answer. After waiting, process 1100 displays a continue button at step 1130, and process 1100 proceeds to step 1135 to check if a response was received. Alternatively, if a response is expected at step 1120, process 1100 advances to step 1135 without waiting and displaying a continue button.

If a response has not been received, step 1135 is NO, and process 1100 checks if a time limit has expired at step 1150. If the time limit, such as fifteen seconds, has not expired, process 1100 again checks if a response has been received at step 1135. Otherwise, if the time limit has expired, step 1150 is NO, and process 110 proceeds to display an exit button at step 1155. The exit button may allow the user or healthcare professional to quit the test session without completing all test screens. Once the exit button is selected at step 1160, process 1100 proceeds to display an incomplete test screen at 1165. The incomplete test screen may include statistics of the completed tests and provide an option to store the visual acuity metric, motor skill metric, and cognitive ability metric calculated for the portion of tests that were completed. In this way, a healthcare professional may avoid losing data and repeating test sessions if the user inadvertently exits or stops the test session after completing some test screens.

Alternatively, if step 1135 is YES, process 1100 proceeds to step 1140 and determines if all repetitions requested of the user have been completed. If step 1140 is NO, repetitions remain, and process 1100 returns to step 1110 to wait and display another test screen. If all repetitions are complete, step 1140 is YES, and process 110 displays a test complete message at step 1145 containing analysis of the test session, such as values of the cognitive ability metric, visual acuity metric, and motor skill metric, a test duration, an accuracy metric, and the like.

It is intended that the disclosure and examples be considered as exemplary only, with a true scope and spirit of disclosed embodiments being indicated by the following claims.

What is claimed is:

1. A system for measuring reaction times of a user, comprising:
   an electronic device comprising a touchscreen, a user-facing camera, at least one memory storing operation instructions, and at least one processor;
   a first sensor device attached to the user, the first sensor device comprising an inertial measurement unit;
   the at least one processor executing the operation instructions to perform operations comprising:
   providing, on the touchscreen, a graphical user interface with at least one selection region;
   updating, at an interval, the graphical user interface to provide at least one object related to the at least one selection region;
   receiving a user selection on the graphical user interface of the touchscreen;
   recording, between the updating and the receiving, data comprising:
   image data, from the user-facing camera, including at least a portion of a face of the user;
   first motion data, from the first sensor device, representing first motions of the user;
   location data, from the touchscreen, representing a location of the user selection within the graphical user interface; and
   time data, indicating a time period between the updating and the receiving;
   determining, based on the location data, if the user performed reaction test instructions comprising selecting one of the at least one selection region on the touchscreen when at least one corresponding object appears;
   calculating, based on the image data, a visual acuity metric as an average percent of a field of view of the camera that includes the user's face;
   calculating, based on the first motion data, a motor skill metric as an average amount of time the user moves between the updating and the receiving;

calculating, based on the time data, a cognitive ability metric as an average time period between the updating and the receiving, comparing the visual acuity metric, the motor skill metric, and the cognitive ability metric to a visual acuity threshold, a motor skill threshold, and a cognitive ability threshold, respectively; and providing, based on the comparing, an alert based on at least one of the following occurring:

the visual acuity metric exceeding the visual acuity threshold, the motor skill metric exceeding the motor skill threshold, or the cognitive ability metric exceeding the cognitive ability threshold.

2. The system of claim 1, wherein the operations further comprise:

storing the visual acuity metric, the motor skill metric, and the cognitive ability metric;

setting a baseline value of visual acuity, a baseline value of motor skill, and a baseline value of cognitive ability as an average of the stored visual acuity metrics, stored motor skill metrics, and stored cognitive ability metrics, respectively; and setting the visual acuity threshold, the motor skill threshold, and the cognitive ability thresholds based on respective baseline values.

3. The system of claim 1, wherein the operations further comprise waiting for a predefined period before updating the graphical user interface.

4. The system of claim 3, wherein the operations further comprise:

providing a user-entry field;

receiving a user entry in the user-entry field; and setting the predefined period to the user entry.

5. The system of claim 1, wherein the operations further comprise waiting for a random period before updating the graphical user interface, wherein the random period is within a predefined range.

6. The system of claim 1, wherein the operations further comprise:

updating the graphical user interface to display the object in a size and a color that differ from a size and color of the object prior to the update; and calculating the visual acuity metric based on the size or color of the objects.

7. The system of claim 1, wherein the operations further comprise:

calculating the motor skill metric based on a number of accelerations in the first motion data that exceed an acceleration threshold.

8. The system of claim 1, wherein the operations further comprise:

updating the graphical user interface to provide a display corresponding to reaction test instructions having a difficulty level, based on a number of objects displayed, that differs from a difficulty level of a previous iteration; and calculating the cognitive ability metric based on the difficulty level of each iteration.

9. The system of claim 1, wherein the operations further comprise:

identifying locations of the user's pupils in the image data;

calculating, based on the user's pupil locations, where the user looks;

calculating, based on where the user looks, an amount of time the user spends looking at the touchscreen; and calculating the cognitive ability metric based on the amount of time the user spends looking at the touchscreen.

10. The system of claim 1, wherein the operations further comprise:

asking if the user is currently wearing eyeglasses;

receiving a user eyeglasses response;

identifying the user's eyeglasses in the image data;

calculating, based on the user's eyeglasses location, where the user looks;

calculating, based on where the user looks, an amount of time the user spends looking at the touchscreen; and calculating the cognitive ability metric based on the amount of time the user spends looking at the touchscreen.

11. The system of claim 1, further comprising:

a second sensor device attached to the user, the second sensor device comprising an inertial measurement unit, the first sensor device being worn on a first hand of the user and the second sensor device being worn on a second hand of the user;

the reaction test instructions further comprise specifying which hand the user must use when selecting the one of the at least one selection region; and the operations further comprise:

recording, between the updating and the receiving, second motion data, from the second sensor device, representing a second motion of the user;

determining if the user performed the reaction test instructions with the correct hand based on the first motion data and second motion data;

calculating, based on the first motion data, a first hand motor skill metric as an average amount of time the user moves between the updating and the receiving when the reaction test instructions specify that the first hand must be used; and calculating, based on the second motion data, a second hand motor skill metric as an average amount of time the user moves between the updating and the receiving when the reaction test instructions specify that the second hand must be used.

12. The system of claim 1, wherein:

the reaction test instructions comprise:

selecting a first selection region when a first object appears; and selecting a second selection region when a second object appears; and the operations further comprise:

providing the graphical user interface with the first selection region and the second selection region;

randomly selecting the first object or the second object;

updating the graphical user interface to provide the randomly selected object;

determining, based on the location data, if the user selected the selection region corresponding to the randomly selected object;

calculating an average correct response time as the average of time periods where the user selected the selection region corresponding to the randomly selected object;

calculating an average incorrect response time as the average, multiplied by a penalty factor, of time periods where the user did not select the selection region corresponding to the randomly selected object; and calculating the cognitive ability metric as an average of the average correct response time and the average incorrect response time.

13. The system of claim 1, wherein:
the reaction test instructions comprise:
selecting a first selection region when a first object appears on a first side of the touchscreen; and
selecting a second selection region when the first object appears on a second side of the touchscreen;
the operations further comprise:
providing the graphical user interface with the first selection region and the second selection region;
randomly selecting the first side or the second side;
updating the graphical user interface to provide the first object on the randomly selected side and a second object on a remaining side;
determining, based on the location data, if the user selected the selection region corresponding to the randomly selected side;
calculating an average correct response time as the average of time periods where the user selected the selection region corresponding to the randomly selected side;
calculating an average incorrect response time as the average, multiplied by a penalty factor, of time periods where the user did not select the selection region corresponding to the randomly selected side; and
calculating the cognitive ability metric as an average of the average correct response time and the average incorrect response time.

14. The system of claim 1, wherein:
the reaction test instructions comprise:
selecting the one of the at least one selection region when a first object appears; and
not selecting the one of the at least one selection region when a second object appears; and
the operations further comprise:
randomly selecting the first object or the second object;
updating the graphical user interface to provide the selected object;
updating the graphical user interface if a time limit expires and the user did not select the one of the at least one selection region.

15. The system of claim 1, wherein:
the reaction test instructions comprise:
selecting the one of the at least one selection region when a number of first objects exceeds a number of second objects; and
not selecting the one of the at least one selection region when the number of first objects is less than the number of second objects; and
the operations further comprise:
randomly selecting the number of first objects and the number of second objects to display on the interface; and
updating the graphical user interface to provide the first objects and the second objects; and
updating the graphical user interface if a time limit expires and the user did not select the one of the at least one selection region.

16. The system of claim 1, wherein the operations further comprise:
updating the graphical user interface to display a test complete message if the graphical user interface has been updated a predefined number of times.

17. The system of claim 1, wherein the operations further comprise:
updating the graphical user interface to provide an incomplete test screen if a time limit has expired and an exit button is selected, the incomplete test screen comprising a save button; and
storing the visual acuity metric, the motor skill metric, and the cognitive ability metric if the save button is selected.

18. The system of claim 1, wherein the operations further comprise:
calculating an average of the time data;
calculating, based on the determining, a correct selection rate as a ratio of a number of correct selections to a number of incorrect selections;
calculating a reaction metric as a quotient of the average time data and the correct selection rate;
calculating, based on the first motion data, a number of accelerations above a threshold;
calculating, based on the image data, a number of times the user looks away from the touchscreen; and
calculating a total score as a sum of the reaction metric, the number of accelerations above the threshold, and the number of times the user looks away.

19. The system of claim 1, wherein
the electronic device further comprises a touchscreen motion sensor;
the reaction test instructions comprise a direction to move the electronic device; and
the operations further comprise:
recording, between the updating and the receiving, data comprising second motion data, from the touchscreen motion sensor, representing second motions of the user;
determining if the user correctly performed the reaction test instructions based on the second motion data; and
calculating the motor skill metric on the basis of a number of accelerations, measured by the touchscreen motion sensor, that exceed an acceleration threshold.

20. The system of claim 1, wherein:
the reaction test instructions comprise a direction that the user must touch a physical item before selecting the one of the at least one selection region; and
the operations further comprise:
determining, based on a number of accelerations of the first motion data, if the user correctly performed the reaction test instructions; and
calculating the motor skill metric based on a number of accelerations above a first acceleration threshold and below a second acceleration threshold.

21. A method for measuring reaction times of a user, comprising:
providing an electronic device comprising a touchscreen and a user-facing camera;
providing a first sensor device attached to the user, the first sensor device comprising an inertial measurement unit;
providing, on the touchscreen, a graphical user interface with at least one selection region;
updating, at an interval, the graphical user interface to provide at least one object related to the at least one selection region;
receiving a user selection on the graphical user interface of the touchscreen;

recording, between the updating and the receiving, data comprising:
- image data, from the user-facing camera, including at least a portion of a face of the user;
- first motion data, from the first sensor device, representing first motions of the user;
- location data, from the touchscreen, representing a location of the user selection within the graphical user interface; and
- time data, indicating a time period between the updating and the receiving;

determining, based on the location data, if the user performed reaction test instructions comprising selecting one of the at least one selection region on the touchscreen when at least one corresponding object appears;

calculating, based on the image data, a visual acuity metric as an average percent of a field of view of the camera that includes the user's face;

calculating, based on the first motion data, a motor skill metric as an average amount of time the user moves between the updating and the receiving;

calculating, based on the time data, a cognitive ability metric as an average time period between the updating and the receiving, comparing the visual acuity metric, the motor skill metric, and the cognitive ability metric to a visual acuity threshold, a motor skill threshold, and a cognitive ability threshold, respectively; and providing, based on the comparing, an alert based on at least one of the following occurring:
- the visual acuity metric exceeding the visual acuity threshold,
- the motor skill metric exceeding the motor skill threshold, or
- the cognitive ability metric exceeding the cognitive ability threshold.

22. A non-transitory computer-readable media storing instructions that, when executed on one or more processors, cause the one or more processors to perform operations for measuring reaction times of a user, comprising:

providing, on a touchscreen of an electronic device, a graphical user interface with at least one selection region;

updating, at an interval, the graphical user interface to provide at least one object related to the at least one selection region;

receiving a user selection on the graphical user interface of the touchscreen;

recording, between the updating and the receiving, data comprising:
- image data, from a user-facing camera, including at least a portion of a face of the user;
- first motion data, from a first sensor device comprising an inertial measurement unit attached to the user, representing first motions of the user;
- location data, from the touchscreen, representing a location of the user selection within the graphical user interface; and
- time data, indicating a time period between the updating and the receiving;

determining, based on the location data, if the user performed reaction test instructions comprising selecting one of the at least one selection region on the touchscreen when at least one corresponding object appears;

calculating, based on the image data, a visual acuity metric as an average percent of a field of view of the camera that includes the user's face;

calculating, based on the first motion data, a motor skill metric as an average amount of time the user moves between the updating and the receiving;

calculating, based on the time data, a cognitive ability metric as an average time period between the updating and the receiving, comparing the visual acuity metric, the motor skill metric, and the cognitive ability metric to a visual acuity threshold, a motor skill threshold, and a cognitive ability threshold, respectively; and providing, based on the comparing, an alert based on at least one of the following occurring:
- the visual acuity metric exceeding the visual acuity threshold,
- the motor skill metric exceeding the motor skill threshold, or
- the cognitive ability metric exceeding the cognitive ability threshold.

* * * * *